US011172658B2

(12) United States Patent
Phelps et al.

(10) Patent No.: US 11,172,658 B2
(45) Date of Patent: Nov. 16, 2021

(54) PORCINE ANIMALS LACKING EXPRESSION OF FUNCTIONAL ALPHA 1, 3 GALACTOSYLTRANSFERASE

(71) Applicant: Revivicor, Inc., Blacksburg, VA (US)

(72) Inventors: Carol J. Phelps, Blacksburg, VA (US); David L. Ayares, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 118 days.

(21) Appl. No.: 15/905,249

(22) Filed: Feb. 26, 2018

(65) Prior Publication Data

US 2018/0332832 A1 Nov. 22, 2018

Related U.S. Application Data

(63) Continuation of application No. 14/281,464, filed on May 19, 2014, now abandoned, which is a continuation of application No. 12/835,026, filed on Jul. 13, 2010, now abandoned, which is a continuation of application No. 10/646,970, filed on Aug. 21, 2003, now Pat. No. 7,795,493.

(60) Provisional application No. 60/404,775, filed on Aug. 21, 2002.

(51) Int. Cl.
*C12N 15/00* (2006.01)
*A01K 67/027* (2006.01)
*C12N 9/40* (2006.01)
*C12N 15/85* (2006.01)

(52) U.S. Cl.
CPC ........ *A01K 67/0276* (2013.01); *C12N 9/2465* (2013.01); *C12N 15/8509* (2013.01); *A01K 2217/075* (2013.01); *A01K 2227/108* (2013.01); *A01K 2267/02* (2013.01); *A01K 2267/025* (2013.01)

(58) Field of Classification Search
USPC .................................................. 800/17, 21
See application file for complete search history.

(56) References Cited

U.S. PATENT DOCUMENTS

| 4,797,368 | A | | 1/1989 | Carter et al. |
| 4,863,852 | A | * | 9/1989 | Wilkins ........... G01N 33/56911 435/7.25 |
| 5,175,383 | A | | 12/1992 | Leder et al. |
| 5,354,768 | A | | 10/1994 | Terada et al. |
| 5,474,935 | A | | 12/1995 | Chatterjee et al. |
| 5,523,226 | A | | 6/1996 | Wheeler |
| 5,681,731 | A | | 10/1997 | Lebkowski et al. |
| 5,714,353 | A | | 2/1998 | Pathak et al. |
| 5,821,117 | A | | 10/1998 | Sandrin et al. |
| 5,849,991 | A | | 12/1998 | d'Apice et al. |
| 5,850,004 | A | | 12/1998 | MacMicking et al. |
| 5,922,601 | A | | 7/1999 | Baetscher et al. |
| 5,942,435 | A | | 8/1999 | Wheeler |
| 6,153,428 | A | * | 11/2000 | Gustafsson ........ A01K 67/0275 424/93.21 |
| 6,235,969 | B1 | | 5/2001 | Stice et al. |
| 6,258,998 | B1 | | 7/2001 | Damiani et al. |
| 6,331,658 | B1 | | 12/2001 | Cooper et al. |
| 6,413,769 | B1 | | 7/2002 | Gustafsson et al. |
| 6,455,037 | B1 | | 9/2002 | Ioannou et al. |
| 6,849,448 | B1 | | 2/2005 | D'Apice et al. |
| 7,126,039 | B2 | | 10/2006 | Denning et al. |
| 2001/0055584 | A1 | | 12/2001 | Mckenzie et al. |
| 2002/0031494 | A1 | | 3/2002 | Sandrin et al. |
| 2002/0152488 | A1 | | 10/2002 | Cooper et al. |
| 2003/0014770 | A1 | | 1/2003 | Gustafsson et al. |
| 2003/0203427 | A1 | | 10/2003 | Koike |
| 2005/0120400 | A1 | | 6/2005 | Day et al. |
| 2006/0242722 | A1 | | 10/2006 | Hawley |

FOREIGN PATENT DOCUMENTS

| EP | 0669829 | 8/2001 |
| JP | 1994-253856 | 9/1994 |
| WO | WO 94/02616 | 2/1994 |
| WO | WO 94/09803 | 5/1994 |
| WO | WO 94/21799 | 9/1994 |
| WO | WO 94/24870 | 11/1994 |
| WO | WO 95/20661 | 8/1995 |
| WO | WO 95/28412 | 10/1995 |
| WO | WO 95/34202 | 12/1995 |
| WO | WO 96/06165 | 2/1996 |
| WO | WO 96/28967 | 9/1996 |
| WO | WO 96/37602 | 11/1996 |
| WO | WO 96/40244 | 12/1996 |
| WO | WO 97/16064 | 5/1997 |
| WO | WO 97/16727 | 5/1997 |
| WO | WO 98/05768 | 2/1998 |
| WO | WO 98/07444 | 2/1998 |
| WO | WO 98/07837 | 2/1998 |
| WO | WO 98/33528 | 8/1998 |
| WO | WO 99/09141 | 2/1999 |

(Continued)

OTHER PUBLICATIONS

Wells et al (Trends Biotechnol 2003:21:428-32) (Year: 2003).*
Yanagimachi (Mol Cell Endocrinol 2002; 187: 241-8) (Year: 2002).*
Kuroiwa et al (Nat Genetics 2004;36:775-80), (Year: 2004).*
Shi et al (Differentiation, ;671(2): 91-113, 2003); (Year: 2003).*
Dinnyes et al, (Cloning and Stem Cells, 4(1): 81-90, 2002) (Year: 2002).*
Wolfhagen (FEMS Microbiology Review, 13 (1994) 59-64); (Year: 1994).*
Galili (Biochimie, 83: 557-563, 2001); (Year: 2001).*
Krueger (JBC, 277(17): 15002-15005, 2002 (Year: 2002).*

(Continued)

*Primary Examiner* — Michael C Wilson
(74) *Attorney, Agent, or Firm* — Foley & Lardner LLP

(57) ABSTRACT

The present invention is a porcine animal, tissue, organ, cells and cell lines, which lack any expression of functional alpha 1,3 galactosyltransferase (alpha1,3GT). These animals, tissues, organs and cells can be used in xenotransplantation and for other medical purposes.

4 Claims, 6 Drawing Sheets
Specification includes a Sequence Listing.

(56) References Cited

FOREIGN PATENT DOCUMENTS

| | | |
|---|---|---|
| WO | WO 99/09163 | 2/1999 |
| WO | WO 99/19469 | 4/1999 |
| WO | WO 99/21415 | 5/1999 |
| WO | WO 99/49029 | 9/1999 |
| WO | WO 00/06194 | 2/2000 |
| WO | WO 00/11147 | 3/2000 |
| WO | WO 00/51424 | 9/2000 |
| WO | WO 01/23541 | 4/2001 |
| WO | WO 01/30992 | 5/2001 |
| WO | WO 02/10337 | 2/2002 |
| WO | WO 02/074935 | 9/2002 |
| WO | WO 03/014770 | 1/2003 |
| WO | WO 03/055302 | 7/2003 |
| WO | WO 2004/016742 | 2/2004 |

OTHER PUBLICATIONS

Whitelaw et al, FEBS Letters, 571: 233-236, 2004.
Oback et al, Cloning and Stem Cells, 4(2): 169-174, 2002.
Shi et al, Differentiation, 671(2): 91-113, 2003.
Dinnyes et al, Cloning and Stem Cells, 4(1): 81-90, 2002.
Hochepied et al, Stem Cells, 22: 441-447, 2004.
Yanagimachi (Mol Cell Endocrinol 2002;187:241-8.
Kuroiwa et al (Nat Genetics 2004;36:775-80.
Platt et al (Nat Biotech Mar. 2002; 20(3)231-2.
Clark et al (Nature Reviews, Genetics, 4 : 825-833, 2003).
Ayares, D., et al., (PPL Therapeutics, Inc.), "Gene targeting in livestock," Transgenic Animal Research Conference (hosted by Univ. of Calif. at Davis biotechnology program, at the Granlibakken Conf. Ctr. in Tahoe City, CA, Jul. 1999 [http:www.biotech.ucdavis.edu]), abstract at p. 20.
Ayares, D., et al., (PPL Therapeutics, Inc.), "Gene targeting in livestock for production of novel biopharmaceuticals," ISB News Report (published by Information Systems for Biotechnology), Nov. 1999:5-6, at http://www.isb.vt.edu/news/1999/Nov44.pdf.
Ayares, D., et al., "Cloning pigs deficient in .alpha.1,3 galactosyltransferase," Graft, 4(1):80-83 (2001).
Bach, F.H., et al., "Delayed xenograft rejection," Immunol. Today, 17(8):379-384 (Aug. 1996).
Betthauser, J., et al., "Production of cloned pigs from in vitro systems," Nature Biotechnology, 18(10):1055-1059 (Oct. 2000).
Bondioli, K., et al., Cloned pigs generated from cultured skin fibroblasts derived from a H-transferase transgenic boar, Molecular Reproduction and Development, 60(2):189-195 (Oct. 2001).
Brandon, E.P., et al., "targeting the mouse genome: A compendium of knockouts (part I)," Current Biology, 5[6]:625-634 (1995).
Brandon, E.P., et al., "targeting the mouse genome: A compendium of knockouts (part II)," Current Biology, 5[7]:758-765 (1995).
Brandon, E.P., et al., "targeting the mouse genome: A compendium of knockouts (part III)," Current Biology, 5[8]:873-881 (1995).
Butler, D., "Xenotransplant experts express caution over knockout piglets," Nature, 415(6868):103-104 (Jan. 10, 2002).
Capecchi, M.R., et al., "Altering the genome by homologous recombination," Science, 244(4910):1288-1292 (Jun. 16, 1989).
Clark, A.J., et al., "Gene targeting in livestock: a preview," Transgenic Res., 9(4-5):263-275 (2000).
Clark, G.F., et al., "Toxin A from Clostridium dificile binds to rabbit erythrocyte glycolipids with terminal Gal alpha 1-3Gal beta 1-4GlcNAc sequences," Arch.Biochem.Biophys., 257(1):217-229, (Aug. 15, 1987).
Cooper, D.K., et al., "Oligosaccharides and discordant xenotransplantation," Immunol. Rev., 141:31-58 (Oct. 1994).
Cooper, D.K.C., et al., "Genetically engineered pigs," Lancet, 342:682-683 (Sep. 11, 1993).
Costa, C., et al., "Expression of the human .alpha.1,2-fucosyltransferase in transgenic pigs modifies the cell surface carbohydrate phenotype and confers resistance to human serum-mediated cytolysis," FASEB J., 13:1762-1773 (Oct. 1999).

Dabkowski, P.L., et al., "Characterisation of a cDNA clone encoding the pig alpha 1,3 galactosyltransferase: implications for xenotransplantation," Transplant Proc., 25(5):2921 (Oct. 1993).
Dabkowski, P.L., et al., "Isolation of a cDNA clone encoding the pig alpha 1,3 galactosyltransferase," Transplant Proc., 26(3):1335 (Jun. 1994).
Dai, Y., et al., "Targeted disruption of the .alpha.1,3-galactosyltransferase gene in cloned pigs," Nature Biotechnology, 20:251-255 (Mar. 2002).
Dalmasso, A.P., et al., "Inhibition of complement-mediated endothelial cell cytotoxicity by decay-accelerating factor: Potential for prevention of xenograft hyperacute rejection," Transplantation, 52(3):530-533 (Sep. 1991).
Dalmasso, A.P., et al., "Reaction of complement with endothelial cells in a model of xenotransplantation," Clin. Exp .Immunol., 86:31-35 (1991).
D'Apice, A.J., et al., "Two genetic approaches to the galactose alpha 1,3 galactose xenoantigen," Transplant Proc., 28(2:540 (Apr. 1996).
Denning, C., et al., "Gene targeting in primary fetal fibroblasts from sheep and pig," Cloning Stem Cells, 3(4):221-231 (2001).
Denning, C., et al., "Deletion of the .alpha.(1,3)galactosyl transferase (GGTA1) gene and the prion protein (PrP) gene in sheep," Nature Biotechnology, 19:559-562 (Jun. 2001).
Fabre, J.W., "Nudging xenotransplantation towards humans," Nature Med., 1(5):403-404 (May 1995).
Galili, U., "The .alpha.-gal epitope (Gala-3Gal.beta.-4GlcNAc-R) in xenotransplantation," Biochimie, 83:557-563 (2001).
Galili, U., et al., "Evolution and pathophysiology of the human natural anti-alpha-galactosyl IgG (anti-Gal) antibody," Springer Semin. Immunopathol., 15(2-3):155-171 (1993).
Galili, U., et al., "Evolutionary relationship between the natural anti-Gal antibody and the Gal alpha 1-3Gal epitope in primates," Proc. Natl. Acad. Sci., U S A., 84(5):1369-1373 (Mar. 1987).
Galili, U., et al., "Human natural anti-alpha-galactosyl IgG. II. The specific recognition of alpha (1-3)-linked galactose residues," J. Exp. Med., 162(2):573-582 (Aug. 1, 1985).
Galili, U., et al., "Man, apes, and old world monkeys differ from other mammals in the expression of .alpha.-galactosyl epitopes on nucleated cells," J.Biol.Chem., 263(33):17755-17762 (Nov. 25, 1988).
Gassmann, M., et al., "Maintenance of an extrachromosomal plasmid vector in mouse embryonic stem cells," Proc. Natl. Acad. Sci. USA, 92(5):1292-1296 (Feb. 28, 1995).
Gastinel, L.N., et.al., "Bovine a1,3-galactosyltransferase catalytic domain structure and its relationship with ABO histo-blood group and glycosphingolipid glycosyltransferases," EMBO Journal, 20(4):638-649 (2001).
Hammer, R.E., et al., "Production of transgenic rabbits, sheep and pigs by microinjection," Nature, 315(6021):680-683 (Jun. 20-26, 1985).
Hancock, W., "Hyde Park Speakers Corner: Xeno-stagnation," AST Newsletter, 6(3):31-33 (Summer 1999) (American Society of Transplantation, Moorestown, NJ) (also published at http://www.a-s-t.org/library/newsArchive/vol6-3/hydepark.htm).
Harduin-Lepers, A., et al., "Characterization of two cis-regulatory regions in the murine beta 1,4-galactosyltransferase gene. Evidence for a negative regulatory element that controls initiation at the proximal site," J. Biol. Chem., 268(19):14348-14359 (Jul. 5, 1993).
Harrison, S.J:, et al., "Efficient generation of .alpha.(1,3) galactosyltransferase knockout porcine fetal fibroblasts for nuclear transfer," Transgenics Research, 11:143-150 (2002).
Hasty, P., et al., "The length of homology required for gene targeting in embryonic stem cells," Mol. Cell Biol.,11(11):5586-5591 (Nov. 1991).
Hayashi, S., et al., "Adenovirus-mediated gene transfer of antisense ribozyme for alpha (1,3)galactosyltransferase gene and alpha (1,2)fucosyltransferase gene in xenotransplantation," Transplant Proc., 29(4):2213 (Jun. 1997).
Hennet, T., "The galatoxyltransferase family," Cell. Mol. Life Sci., 59:1081-1095 (2002).
Joyner, A.L., "Production of a mutation in mouse En-2 gene by homologous recombination in embryonic stem cells," Nature, 338(6211)::153-156 (Mar. 9, 1989).

(56) References Cited

OTHER PUBLICATIONS

Joziasse, D.H., et al., "Bovine .alpha.1.fwdarw.3-galactosyltransferase: Isolation and characterization of a cDNA clone: Identification of homologous sequences in human genomic DNA," J. Biol. Chem., 264(24):14290-14297 (Aug. 25, 1989).
Joziasse, D.H., et al., "Characterization of an .alpha.1.fwdarw.3-galactosyltransferase homologue on human chromosome 12.that is organized as a processed pseudogene," The Journal of Biological Chemistry, 266(11):6991-6998 (Apr. 15, 1991).
Joziasse, D.H., et al., "Murine .alpha.1.fwdarw.3-galactosyltransferase: A single gene locus specifies four isoforms of the enzyme by alternative splicing," J. Biol. Chem., 267(8) 5534-5541 (Mar. 15, 1992).
Joziasse, D.H., et al., "Xenotransplantation: the importance of the Galalpha1,3Gal epitope in hyperacute vascular rejection," Biochim. Biophys. Acta, 1455(2-3):403-418 (Oct. 8, 1999).
Just, I., et al., "The low molecular mass GTP-binding protein rho is affected by toxin A from Clostridium difficile," J. Clin. Invest., 95:1026-1031 (1995).
Katayama, A., et al., "Porcine .alpha.-1,3-galactosyltransferase: full length cDNA cloning, genomic organization, and analysis of splicing variants," Glyconjugate Journal, 15:583-589 (1998).
Kelly, R.J., et al., "Sequence and expression of a candidate for the human Secretor blood group alpha (1,2)fucosyltransferase gene (FUT2). Homozygosity for an enzyme-inactivating nonsense mutation commonly correlates with the non-secretor phenotype," J. Biol. Chem., 270(9):4640-4649 (Mar. 3, 1995).
Kilby, N.J., et al., "Site-specific recombinases: tools for genome engineering," Trends in Genetics, 9(12):413-421 (Dec. 1993).
Koike, C., et al., "Comparison of the regulatory regions of the of .alpha.1,3galactosyltransferase gene between murine and porcine species," Transplantation Proceedings, 33:710-711 (2001).
Koike, C., et al., "Direct gene replacement of the mouse .alpha.(1,3)-galactosyltransferase gene with human .alpha.(1,2)-fucosyltransferase gene: Converting .alpha.-galactosyl epitopes into H antigens," Xenotransplantation, 4:147-153 (1997).
Koike, C., et al., "Introduction of .alpha.(1,2)-fucosyltransferase and its effect on .alpha.-Gal epitopes in transgenic pig," Xenotransplantation, 3:81-86 (1996).
Koike, C., et al., "Isolation of the regulatory regions and genomic organization of the porcine .alpha.1,3-galactosyltransferase gene," Transplantation, 70(9):1275-1283 (Nov. 15, 2000).
Koike, C., et al., "Molecular basis of evolutionary loss of the .alpha.1,3-galactosyltransferase gene in higher primates," J. Biol. Chem., 277(12):10114-101120 (Mar. 22, 2002).
Lai, L., et al., "Production of .alpha.-1,3-galactosyltransferase knock-out pigs by nuclear transfer cloning," Science 295:1089-1092 (Feb. 8, 2002) and supplementary data, Science Express, Jan. 3, 2002.
Larsen, R.D., et al., "Frameshift and nonsense mutations in a human genomic sequence homologous to a murine UDP-Gal:beta-D-Gal(1,4)-D-GlcNAc alpha(1,3)-galactosyltransferase cDNA," J. Biol. Chem., 265(12):7055-7061 (Apr. 25, 1990).
Larsen, R.D., et al., "Isolation of a cDNA encoding a murine UDPgalactose:beta-D-galactosyl-1,4-N-acetyl-D-glucosaminide alpha-1,3-galactosyltransferase: expression cloning by gene transfer," Proc. Natl. Acad. Sci., U S A., 86(21):8227-8231 (Nov. 1989).
Larsen, R.D., et al., "Molecular cloning, sequence, and expression of a human GDP-L-fucose:beta-D-galactoside 2-alpha-L-fucosyltransferase cDNA that can form the H blood group antigen," Proc. Natl. Acad. Sci., U S A., 87(17):6674-6678 (Sep. 1990).
Lo, N.W., et al., "Transcription of the beta-galactoside alpha 2,6-sialyltransferase gene in B lymphocytes is directed by a separate and distinct promoter," Glycobiology, 6(3):271-279 (Apr. 1996).
Luckow, V.A., et al., "Trends in the development of baculovirus expression vector," Bio/Technology, 6:47-55 (Jan. 1988).
Mansour, S.L., et al., "Disruption of the proto-oncogene int-2 in mouse embryo-derived stem cells: a general strategy for targeting mutations to non-selectable genes," Nature, 336(6197:348-352 (Nov. 24, 1988).

McCarrick, J.W. 3rd, et al., "Positive-negative selection gene targeting with the diphtheria toxin A-chain gene in mouse embryonic stem cells," Transgenic Res., 2(4):183-190 (Jul. 2, 1993).
McCreath, K.J., et al., "Production of gene-targeted sheep by nuclear transfer from somatic cells," Nature, 405:1066-1069 (Jul. 29, 2000).
McCurry, K.R., et al., "Human complement regulatory proteins protect swine-to-primate cardiac xenografts from humoral injury," Nature Med. 1(5):423-427 (May 1995).
McKenzie, I.F., et al., "Strategies to overcome the anti-Gal alpha (1-3)Gal reaction in xenotransplantation," Transplant Proc., 28(2):537 (Apr. 1996).
Miyagawa, S., et al., "Remodeling of the major pig xenoantigen by N-acetylglucosaminyltransferase III in transgenic pig," J. Biol. Chem., 276(42):39310-39319 (Oct. 19, 2001).
Moreadith, R.W., et al., "Gene targeting in embryonic stem cells: the new physiology and metabolism," J. Mol. Med., 75(3):208-216 (Mar. 1997).
Mueller, S., et al., "Chimeric pigs following blastocyst injection of transgenic porcine primordial germ cells," Mol. Reprod. Dev., 54(3):244-254 (Nov. 1999). cited by other.
Mullins, L.J., et al., "Transgenesis in the rat and larger mammals," J. Clin. Invest., 97(7):1557-1560 (Apr. 1, 1996).
Nagasaka, T., et al., "Inhibitory effect of .alpha.(1,2) fucosyltransferase recombinant adenoviral vector on .alpha.Gal expression," Transplantation Proceedings, 30:3837-3838 (1998).
Onishi, A., et al., "Pig cloning by microinjection of fetal fibroblast nuclei," Science, 289:1188-1190 (Aug. 18, 2000).
Osman, N., et al., "Combined transgenic expression of alpha-galactosidase and alpha1,2-fucosyltransferase leads to optimal reduction in the major xenoepitope Galalpha(1,3)Gal," Proc. Natl. Acad. Sci. U S A., 94(26):14677-14682 (Dec. 23, 1997).
Pera, M.F., et al., "Human embryonic stem cells," J. Cell. Sci., 113 (Pt 1):5-10 (Jan. 2000).
Phelps, C.J., et al., "Production of .alpha.1,3-galactosyltransferase-deficient pigs," Science, 299:411-414 (Jan. 17, 2003).
Polejaeva, I.A., "Cloning pigs: advances and applications," Reprod., 58 (Suppl.):293-300 (2001).
Polejaeva, I.A., et al., "Cloned pigs produced by nuclear transfer from adult somatic cells," Nature, 407:86-90 (Sep. 7, 2000).
Porter, A.C.G., et al., "Gene Targeting: Techniques and applications to transplantation," Transplantation, 64:1227-1235 (Nov. 15, 1997).
Pray, L., "Refining transgenic mice," The Scientist 16(13):34 (Jun. 24, 2002) [http://www.the-scientist.com/yr2002/jun/profile2.sub.--020624.html- ].
Pursel V.G., et al., "Progress on gene transfer in farm animals," Vet. Immunol. Immunopathol., 17(1-4):303-312 (Dec. 1987).
Ramsoondar, J.J., et al., "Production of .alpha.1,3-galactosyltransferase-knockout cloned pigs expressing human .alpha.1,2-fucosyltransferase," Biol. of Reproduction, 69:437-445 (online before print Apr. 2, 2003).
Rexroad, C.E. Jr., et al., "Production of transgenic sheep with growth-regulating genes," Mol. Reprod. Dev., 1(3):164-169 (1989).
Rexroad, C.E. Jr., et al., "Insertion, expression and physiology of growth-regulating genes in ruminants," J. Reprod. Fert., 41 (Suppl.):119-124 (1990).
Rubnitz, J., et al., "The minimum amount of homology required for homologous recombination in mammalian cells," Mol. Cell. Biol., 4(11):2253-2258 (Nov. 1984).
Sandrin, M.S., et al., Identification of Gal(.alpha.1,3)Gal as the major epitope for pig-to-human vascularized xenografts, Transplant Rev., 8(3):134-139 (Jul. 1994).
Sandrin, M.S., et al., "Characterization of cDNA clones for porcine .alpha.(1,3)galactosyl transferase: The enzyme generating the Gal.alpha.(1,3)Gal epitope," Xenotransplantation, 1:81-88 (1994).
Sao, H., et al., "A new marrow T cell depletion method using anti-CD6 mnoclonal antibody-conjugated magnetic beads and its clinical application for prevention of acute graft-vs.-host disease in allogenic bone marrow transplantation: Rrsults of a phase I-II trial," Intl. J. Hematol., 69(1):27-35 (Jan. 1999).
Sasaki, K., et al., "Expression cloning of a novel Gal beta (1-3/1-4) GlcNAc alpha 2,3-sialyltransferase using lectin resistance selection," J. Biol. Chem., 268(30):22782-22787 (Oct. 25, 1993).

(56) References Cited

OTHER PUBLICATIONS

Shaper, N.L., et al., "Characterization of the full length cDNA for murine beta-1,4-galactosyltransferase. Novel features at the 5'-end predict two translational start sites at two in-frame AUGs," J. Biol. Chem., 263(21):10420-10428 (Jul. 25, 1988).
Sharma, A., et al., "Pig cells that lack the gene for .alpha.1,3-galactosyltransferase express low levels of the gal antigen," Transplantation, 75(4):430-436 (Feb. 7, 2003).
Simons, J.P., et al., "Gene transfer into sheep," Bio/Technology, 6(1):179-183 (Jan. 1988).
Smith, C.M., "Technical knockout: Gene-targeting strategies provide an avenue for studying gene function,"The Scientist,14(15):32 (Jul. 24, 2000) www.the-scientist.com/yr2000/jul/profile.sub.--000724.html.
Starzl, T.E., et al., "Antigen localization and migration in immunity and tolerance," N. Engl. J. Med., 339(26):1905-1913 (Dec. 24, 1998).
Starzl, T.E., et al., "The biological basis of and strategies for clinical xenotransplantation," Immunol. Rev., 141:213-244 (Oct. 1994).
Starzl, T.E., et al., "Will xenotransplantation ever be feasible?" J. Am. Coll. Surg., 186(4):383-387 (Apr. 1998).
Stolberg, S.G., "Could this pig save your life?" N. Y. Times Magazine., Oct. 3, 1999, pp. 46-51.
Stone, K.R., et al., "Porcine and bovine cartilage transplants in cynomolgus monkey," Transplantation, 63(5):640-645 (Mar. 15, 1997).
Strahan, K., et al., "Pig alpha 1,3galactosyltransferase: A major target for genetic manipulation in xenotransplantation," Frontiers in Bioscience, 1:e34-41 (Jul. 1, 1996) [www.bioscience.org/1996/v1/e/strahan1/htmls/34-41.htm].
Strahan, K.M., et al., "cDNA sequence and chromosome localization of pig alpha 1,3 galactosyltransferase," Immunogenetics, 41(2-3):101-105 (1995).
Strahan, K.M., et al., "Pig alpha 1, 3galactosyltransferase: sequence of a full-length cDNA clone, chromosomal localisation of the corresponding gene, and inhibition of expression in cultured pig endothelial cells," Transplant Proc., 27(1):245-246 (Feb. 1995).
Svensson, E.C., et al., "Organization of the beta-galactoside alpha 2,6-sialyltransferase gene. Evidence for the transcriptional regulation of terminal glycosylation," J. Biol. Chem.. 265(34):20863-20868 (Dec. 5, 1990).
Svensson, E.C., et al., "Regulated expression of alpha 2,6-sialyltransferase by the liver-enriched transcription factors HNF-1, DBP, and LAP," J. Biol. Chem..267(5):3466-3472 (Feb. 15, 1992).
Tanemura, M., et al., "Differential expression of the .alpha.-gal epitopes (Gal.alpha.1-3Gal.beta.1-4G1cNAc-R) on pig and mouse organs," 69(1):187-190 (Jan. 15, 2000).
Tanemura, M., et al., "Reduction of the major swine xenoantigen, the .alpha.-galactosyl epitope by transfection of the .alpha.2,3-sialyltransferase gene," J..Biol.Chem., 273(26):16421-16425 (Jun. 26, 1998).
Tearle, R.G., et al., "The .alpha.-1,3-galactosyltransferase knockout mouse," Transplantation, 61(1):13-19 (Jan. 15, 1996).

Thall, A.D., et al., "Oocyte gal.alpha.1,3gal epitopes implicated in sperm adhesion to the Zona pellucida glycoprotein ZP3 are not required for fertilization in the mouse," J. Biol. Chem., 270(27):21437-21440 (Sep. 15, 1995).
Thomas, K.R., et al., "Site-directed mutagenesis by gene targeting in mouse embryo-derived stem cells," Cell, 51(3):503-512 (Nov. 6, 1987).
Vanhove, B., et al., "Porcine .alpha.1,3-galactosyltransferase: Tissue-specific and regulated expression of splicing isoforms," Biochim. Biophys. Acta, 1356(1):1-11 (Mar. 27, 1997).
Vanhove, B., et al., "Transcriptional and posttranscriptional regulation of .alpha.1,3-galactosyltransfer-ase in activated endothelial cells results in decreased expression of Gal.alpha.1,3Gal," Glycobiology, 8(5):481-487 (May 1998).
Vanhove, B., et al., "Variability of alpha 1,3-galactosyltransferase splicing isoforms in pig tissues," Transplant Proc. 28(2):622-623 (Apr. 1996).
Vaughan, H.A., et al., "Gal alpha(1,3)Gal is the major xenoepitope expressed on pig endothelial cells recognized by naturally occurring cytotoxic human antibodies," Transplantation, 58(8):879-882 (Oct. 27, 1994).
Vize, P.D., et al., "Introduction of a porcine growth hormone fusion gene into transgenic pigs promotes growth," J. Cell Sci.,;90 ( Pt 2):295-300 (Jun. 1988).
Wagner, "Development of transgenic pigs," J. Cellular Biochem., 13B (Suppl.):164 (1989) (Abstract).
Weinstein, J., et al., "Primary structure of beta-galactoside alpha 2,6-sialyltransferase. Conversion of membrane-bound enzyme to soluble forms by cleavage of the NH2-terminal signal anchor," .J. Biol. Chem., 262(36):17735-17743 (Dec. 25, 1987).
White, D.J.G., et al., "Expression of human decay accelerating factor or membrane cofactor protein genes on mouse cells inhibits lysis by human complement," Transplant International, 5(Suppl. 1):S648-S650 (1992).
Yamamoto, F.-i., et al., "Genomic organization of human histo-blood group ABO genes," Glycobiology, 5(1):51-58 (1995).
Ye, Y., et al., "Evidence that intravenously administered a-galactosyl carbohydrates reduce baboon serum cytotoxicity to pig kidney cells (PK15) and transplanted pig hearts," Transplantation, 58(3):330-337 (Aug. 15, 1994).
Yarema, K. et al., "Characterizing glycosylation pathways," Genome Biology, 2(5):1-10 (May 1, 2001).
Castagliuolo, I. et al., "Clostridium difficile toxin a carboxyl-terminus peptide lacking ADP-ribosyltransferase activity acts as a mucosal adjuvant," Infection and Immunity, 72(5):2827-2836, (May 2004).
Tanemura et al., "Elimination of anti-Gal B cells by alpha-gal ricin", Transplantation (Baltimore), vol. 73, No. 12, Jun. 27, 2002, pp. 1859-1868, XP002336897 ISSN: 0041-1337.
Thall, "Generation of alpha 1,3galactosyltransferase deficient mice.", Sub-Cellular Biochemistry. 1999, vol. 32, 1999, pp. 259-279, XP009050922 ISSN: 0306-0225.
Stone et al., "Porcine Cartilage Transplants in the Cynomolgus Monkey," Transplantation, Jun. 27, 1998, 65(12):1577-1583.

* cited by examiner

Figure 2

|  |  |  | Exon 9 → |  |
|---|---|---|---|---|
|  | Exon 8 |  | Tyr Ile Glu His Tyr | (SEQ ID NO: 3) |
| Wild type | gct gtc gga ag | A | Tac ATT GAG CAT TAC |  |
|  | (SEQ ID NO: 1) |  | (SEQ ID NO: 2) |  |

|  |  |  | Exon 9 → |  |
|---|---|---|---|---|
|  | Exon 8 |  | Asp Ile Glu His Tyr | (SEQ ID NO: 5) |
| Mutation | gct gtc gga ag | A | Gac ATT GAG CAT TAC |  |
|  | (SEQ ID NO: 1) |  | (SEQ ID NO: 4) |  |

PORCINE ANIMALS LACKING EXPRESSION OF FUNCTIONAL ALPHA 1, 3 GALACTOSYLTRANSFERASE

CROSS REFERENCE TO RELATED APPLICATIONS

This application is a continuation of and claims priority to U.S. application Ser. No. 14/281,464, titled, "Porcine Animals Lacking Any Expression of Functional Alpha 1,3 Galactosyltransferase," filed May 19, 2014, which is a continuation of U.S. application Ser. No. 12/835,026, titled, "Porcine Animals Lacking Any Expression of Functional Alpha 1,3 Galactosyltransferase," filed Jul. 13, 2010, which is a continuation of and claims priority to U.S. application Ser. No. 10/646,970, titled, "Porcine Animals Lacking Any Expression of Functional Alpha 1,3 Galactosyltransferase," filed on Aug. 21, 2003, which granted on Sep. 14, 2010, as U.S. Pat. No. 7,795,493, which claims priority to U.S. Provisional Application No. 60/404,775 filed Aug. 21, 2002. The entire contents of the foregoing applications are hereby incorporated herein by reference.

FIELD OF THE INVENTION

The present invention are porcine animals, tissue and organs as well as cells and cell lines derived from such animals, tissue and organs, which lack any expression of functional alpha 1,3 galactosyltransferase (alpha1,3GT). Such animals, tissues, organs and cells can be used in research and in medical therapy, including in xenotransplantation.

BACKGROUND OF THE INVENTION

Patients with end stage organ failure require organ transplantation for survival. The major limiting factor in clinical transplantation is the shortage of suitable human donors. Over the past ten years the size of the waiting list of patients for organs has increased dramatically, from approximately 30,000 in 1991 to approximately 80,000 in 2001 (Source: New York Organ Donor Network; Association of Organ Procurement Organizations' Death Record Review Study from 1997 to 1999, provided by 30 organ procurement organizations). Despite this increasing need over the past ten years, the number of organ donations has remained flat (approximately 20,000 per year).

According to the United Network for Organ Sharing (UNOS) as of Jul. 17, 2003, there were 82,249 patients waiting for organ transplants in the United States. The need for specific organs was as follows:

| | |
|---|---|
| Kidney | 55,133 |
| Liver | 17,304 |
| Pancreas | 1,413 |
| Kidney and Pancreas | 2,378 |
| Intestine | 173 |
| Heart | 3,717 |
| Heart-Lung | 184 |
| Lung | 3,912 |

Across the U.S., an average of 17 men, women and children of all races and ethnic backgrounds die every day for lack of donated organs, thus, each year, more than 6,200 Americans die waiting for an organ transplant. A need for a more reliable and unlimited source of organs has led to investigation of the potential for transplantation of organs from other animals, referred to as xenotransplantation.

Pigs are considered the most likely source of xenograft organs. The supply of pigs is plentiful, breeding programs are well established, and their size and physiology are compatible with humans. Xenotransplantation, however, presents its own set of problems. The most significant is immune rejection. The first immunological hurdle is "hyperacute rejection" (HAR). HAR can be defined by the ubiquitous presence of high titers of pre-formed natural antibodies binding to the foreign tissue. The binding of these natural antibodies to target epitopes on the donor organ endothelium is believed to be the initiating event in HAR. This binding, within minutes of perfusion of the donor organ with the recipient blood, is followed by complement activation, platelet and fibrin deposition, and ultimately by interstitial edema and hemorrhage in the donor organ, all of which cause failure of the organ in the recipient (Strahan et al. (1996) Frontiers in Bioscience 1, e34-41).

Except for Old World monkeys, apes and humans, most mammals carry glycoproteins on their cell surfaces that contain galactose alpha 1,3-galactose (Galili et al., J. Biol. Chem. 263: 17755-17762, 1988). Humans, apes and Old World monkeys have a naturally occurring anti-alpha gal antibody that is produced in high quantity (Cooper et al., Lancet 342:682-683, 1993). It binds specifically to glycoproteins and glycolipids bearing galactose alpha-1,3 galactose.

In contrast, glycoproteins that contain galactose alpha 1,3-galactose are found in large amounts on cells of other mammals, such as pigs. This differential distribution of the "alpha-1,3 GT epitope" and anti-Gal antibodies (i.e., antibodies binding to glycoproteins and glycolipids bearing galactose alpha-1,3 galactose) in mammals is the result of an evolutionary process which selected for species with inactivated (i.e. mutated) alpha-1,3-galactosyltransferase in ancestral Old World primates and humans. Thus, humans are "natural knockouts" of alpha1,3GT. A direct outcome of this event is the rejection of xenografts, such as the rejection of pig organs transplanted into humans initially via HAR.

A variety of strategies have been implemented to eliminate or modulate the anti-Gal humoral response caused by porcine xenotransplantation, including enzymatic removal of the epitope with alpha-galactosidases (Stone et al., Transplantation 63: 640-645, 1997), specific anti-gal antibody removal (Ye et al., Transplantation 58: 330-337, 1994), capping of the epitope with other carbohydrate moieties, which failed to eliminate alpha-1,3-GT expression (Tanemura et al., J. Biol. Chem. 27321: 16421-16425, 1998 and Koike et al., Xenotransplantation 4: 147-153, 1997) and the introduction of complement inhibitory proteins (Dalmasso et al., Clin. Exp. Immunol. 86: 31-35, 1991, Dalmasso et al. Transplantation 52:530-533 (1991)). C. Costa et al. (FASEB J 13, 1762 (1999)) reported that competitive inhibition of alpha-1,3-GT in H-transferase transgenic pigs results in only partial reduction in epitope numbers. Similarly, S. Miyagawa et al. (J. Biol. Chem 276, 39310 (2001)) reported that attempts to block expression of gal epitopes in N-acetylglucosaminyltransferase III transgenic pigs also resulted in only partial reduction of gal epitopes numbers and failed to significantly extend graft survival in primate recipients.

Single allele knockouts of the alpha-1,3-GT locus in porcine cells and live animals have been reported. Denning et al. (Nature Biotechnology 19: 559-562, 2001) reported the targeted gene deletion of one allele of the alpha-1,3-GT gene in sheep. Harrison et al. (Transgenics Research 11: 143-150, 2002) reported the production of heterozygous alpha-1,3-GT knock out somatic porcine fetal fibroblasts cells. In 2002, Lai et al. (Science 295: 1089-1092, 2002) and Dai et al. (Nature Biotechnology 20: 251-255, 2002) reported the production of pigs, in which one allele of the alpha-1,3-GT gene was successfully rendered inactive. Ramsoondar et al. (Biol of Reproduc 69, 437-445 (2003) reported the generation of heterozygous alpha-1,3-GT knockout pigs that also express human alpha-1,2-fucosyltransferase (HT), which expressed both the HT and alpha-1,3-GT epitopes.

PCT publication No. WO 94/21799 and U.S. Pat. No. 5,821,117 to the Austin Research Institute; PCT publication No. WO 95/20661 to Bresatec; and PCT publication No. WO 95/28412, U.S. Pat. Nos. 6,153,428, 6,413,769 and US publication No. 2003/0014770 to BioTransplant, Inc. and The General Hospital Corporation provide a discussion of the production of alpha-1,3-GT negative porcine cells based on knowledge of the cDNA of the alpha-1,3-GT gene (and without knowledge of the genomic organization or sequence). However, there was no evidence that such cells were actually produced prior to the filing date of these applications and the Examples were all prophetic.

The first public disclosure of the successful production of a heterozygous alpha-1,3-GT negative porcine cell occurred in July 1999 at the Lake Tahoe Transgenic Animal Conference (David Ayares, et al., PPL Therapeutics, Inc.). Prior to the present invention, no one had published or publicly disclosed the production of a homozygous alpha 1,3GT negative porcine cell. Further, since porcine embryonic stem cells have not been available to date, there was and still is no way to use an alpha-1,3-GT homogygous embryonic stem cell to attempt to prepare a live homogygous alpha-1,3-GT knock out pig.

On Feb. 27, 2003, Sharma et al. (Transplantation 75:430-436 (2003) published a report demonstrating a successful production of fetal pig fibroblast cells homozygous for the knockout of the alpha-1,3-GT gene.

PCT publication No. WO 00/51424 to PPL Therapeutics describes the genetic modification of somatic cells for nuclear transfer. This patent application discloses the genetic disruption of the alpha-1,3-GT gene in porcine somatic cells, and the subsequent use of the nucleus of these cells lacking at least one copy of the alpha-1,3-GT gene for nuclear transfer.

U.S. Pat. No. 6,331,658 to Cooper & Koren claims but does not confirm any actual production of genetically engineered mammals that express a sialyltransferase or a fucosyltransferase protein. The patent asserts that the genetically engineered mammals would exhibit a reduction of galactosylated protein epitopes on the cell surface of the mammal.

PCT publication No. WO 03/055302 to The Curators of the University of Missouri confirms the production of heterozygous alpha 1,3GT knockout miniature swine for use in xenotransplantation. This application is generally directed to a knockout swine that includes a disrupted alpha-1,3-GT gene, wherein expression of functional alpha-1,3-GT in the knockout swine is decreased as compared to the wildtype. This application does not provide any guidance as to what extent the alpha-1,3-GT must be decreased such that the swine is useful for xenotransplantation. Further, this application does not provide any proof that the heterozygous pigs that were produced exhibited a decreased expression of functional alpha1,3GT. Further, while the application refers to homozygous alpha 1,3GT knockout swine, there is no evidence in the application that any were actually produced or producible, much less whether the resultant offspring would be viable or phenotypically useful for xenotransplantation.

Total depletion of the glycoproteins that contain galactose alpha 1,3-galactose is clearly the best approach for the production of porcine animals for xenotransplantation. It is theoretically possible that double knockouts, or the disruption of both copies of the alpha 1,3GT gene, could be produced by two methods: 1) breeding of two single allele knockout animals to produce progeny, in which case, one would predict based on Mendelian genetics that one in four should be double knockouts or 2) genetic modification of the second allele in a cell with a pre-existing single knockout. In fact, this has been quite difficult as illustrated by the fact that while the first patent application on knock-out porcine cells was filed in 1993, the first homozygous alpha 1,3GT knock out pig was not produced until July 2002 (which was based on the work of the present inventor and described herein).

Transgenic mice (not pigs) have historically been the preferred model to study the effects of genetic modifications on mammalian physiology, for a number of reasons, not the least of which is that mouse embryonic stem cells have been available while porcine embryonic stem cells have not been available. Mice are ideal animals for basic research applications because they are relatively easy to handle, they reproduce rapidly, and they can be genetically manipulated at the molecular level. Scientists use the mouse models to study the molecular pathologies of a variety of genetically based diseases, from colon cancer to mental retardation. Thousands of genetically modified mice have been created to date. A "Mouse Knockout and Mutation Database" has been created by BioMedNet to provide a comprehensive database of phenotypic and genotypic information on mouse knockouts and classical mutations (http://research.bmn.com/mkmd; Brandon et al Current Biology 5[7]:758-765 (1995); Brandon et al Current Biology 5[8]:873-881 (1995), this database provides information on over 3,000 unique genes, which have been targeted in the mouse genome to date.

Based on this extensive experience with mice, it has been learned that transgenic technology has some significant limitations. Because of developmental defects, many genetically modified mice, especially null mice created by gene knock out technology die as embryos before the researcher has a chance to use the model for experimentation. Even if the mice survive, they can develop significantly altered phenotypes, which can render them severely disabled, deformed or debilitated (Pray, Leslie, *The Scientist* 16[13]: 34(2002); Smith, *The Scientist* 14[15]:32, (2000); Brandon et al., *Current Biology* 5[6]:625-634 (1995); Brandon et al., *Current Biology* 5[7]:758-765 (1995); Brandon et al., *Current Biology* 5[8]:873-881 (1995); research.bmn.com/mkmd). Further, it has been learned that it is not possible to predict whether or not a given gene plays a critical role in the development of the organism, and, thus, whether elimination of the gene will result in a lethal or altered phenotype, until the knockout has been successfully created and viable offspring are produced.

Mice have been genetically modified to eliminate functional alpha-1,3-GT expression. Double-knockout alpha-1,3-GT mice have been produced. They are developmentally viable and have normal organs (Thall et al. J Biol Chem 270:21437-40 (1995); Tearle et al. Transplantation 61:13-19 (1996), see also U.S. Pat. No. 5,849,991). However, two phenotypic abnormalities in these mice were apparent. First, all mice develop dense cortical cataracts. Second, the elimination of both alleles of the alpha-1,3-GT gene significantly affected the development of the mice. The mating of mice heterozygous for the alpha-1,3-GT gene produced genotype ratios that deviated significantly from the predicted Mendelian 1:2:1 ratio (Tearle et al. Transplantation 61:13-19 (1996)).

Pigs have a level of cell surface glycoproteins containing galactose alpha 1,3-galactose that is 100-1000 fold higher than found in mice. (Sharma et al. Transplantation 75:430-436 (2003); Galili et al. Transplantation 69:187-190 (2000)). Thus, alpha1,3-GT activity is more critical and more abundant in the pig than the mouse.

Despite predictions and prophetic statements, prior to this invention, no one knew whether the disruption of both alleles of the alpha-1,3-GT gene would be lethal or would effect porcine development or result in an altered phenotype (Ayares et al. Graft 4(1)80-85 (2001); Sharma et al. Transplantation 75:430-436 (2003); Porter & Dallman Transplantation 64:1227-1235 (1997); Galili, U. Biochimie 83:557-563 (2001)). Indeed, many experts in the field expressed serious doubts as to whether homozygous alpha-1,3-GT knockout pigs would be viable at all, much less develop normally. Such concerns were expressed up until the double knockout pig of the present invention was produced. Examples of statements by those working in the field at the time included the following.

"The abundantly expressed alpha-gal epitope may have some biological roles in pig development, such as in cell-cell interaction. If this assumption is correct, pigs may not develop in the absence of this epitope (Galili, U. Biochimie 83:557-563 (2001)."

"The inability to generate knockout pigs for alpha-gal may suggest that alpha-gal epitopes are indispensable in this species (Galili et al. Transplantation 69:187-190 (2000))."

"Although double-knockout alpha-gal mice develop and remain fairly normal, the possibility exists that deletion of this enzyme could have more severe consequences in other animals (Porter & Dallman Transplantation 64:1227-1235 (1997))."

"It is possible that the GT(−/−) pig may not be viable because the GT gene is essential for embryonic development. An answer to this question and to the relevance of GT(−/−) pigs to xenotransplantation research must await, if possible, the production of the appropriate pigs (Sharma et al. Transplantation 75:430-436 (2003))."

"Since Gal epitope expression in pig organs is up to 500-fold higher than in mouse organs, there is the possibility that alphaGT activity is more crucial to the pig and could effect development of these pigs (Ayares et al. Graft 4(1) 80-85 (2001))."

Thus, until a viable double alpha-1,3-GT knockout pig is produced, according to those of skill in the art at the time, it was not possible to determine (i) whether the offspring would be viable or (ii) whether the offspring would display a phenotype that allows the use of the organs for transplantation into humans.

It is therefore an object of the present invention to provide viable pigs which lack any expression of functional alpha1,3GT.

It is another object of the present invention to provide procine cells, tissues and organs, which lack any expression of functional alpha1,3GT, for use in xenotransplantation or other biomedical applications.

It is a further object of the present invention to provide a method to select and screen for porcine cells, which lack galactose alpha 1,3-galactose epitopes on the cell surface.

SUMMARY OF THE INVENTION

This invention is the production of the first live pigs lacking any functional expression of alpha 1,3 galactosyltransferase. The subject of this invention was heralded in a full paper in Science magazine in 2003 (Phelps et al. (Science 299:411-414 (2003)) and widely reported in the press as a breakthrough in xenotransplantation.

It has for the first time been proven that a viable porcine animal that lacks any expression of functional alpha 1,3 galactosyltransferase can be produced. The present invention provides the complete inactivation of both alleles of the alpha 1,3 galactosyltransferase gene in pigs, thus overcoming this longstanding hurdle and making xenotransplantation a reality. Eliminating the expression of this gene, resulting in a lack of galactose alpha 1,3-galactose epitopes on the cell surface, represents the first and major step in eliminating hyperacute rejection in pig-to-human xenotransplantation therapy. The invention also provides organs, tissues, and cells derived from such porcine animals, which are useful for xenotransplantation.

In embodiments of the present invention, the alleles of the alpha-1,3-GT gene are rendered inactive, such that the resultant alpha-1,3-GT enzyme can no longer generate galactose alpha1,3-galactose on the cell surface. In one embodiment, the alpha-1,3-GT gene can be transcribed into RNA, but not translated into protein. In another embodiment, the alpha-1,3-GT gene can be transcribed in an inactive truncated form. Such a truncated RNA may either not be translated or can be translated into a nonfunctional protein. In an alternative embodiment, the alpha-1,3-GT gene can be inactivated in such a way that no transcription of the gene occurs. In a further embodiment, the alpha-1,3-GT gene can be transcribed and then translated into a nonfunctional protein.

In another embodiment, pigs that lack any expression of functional alpha-1,3-GT are useful for providing a clearer evaluation of approaches currently in development aimed at overcoming potential delayed and chronic rejection mechanisms in porcine xenotransplantation.

In one aspect of the present invention, porcine animals are provided in which at least one allele of the alpha-1,3-GT gene is inactivated via a genetic targeting event. In another aspect of the present invention, porcine animals are provided in which both alleles of the alpha-1,3-GT gene are inactivated via a genetic targeting event. The gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knockout") or insertion ("knockin") techniques. Additional genes for a desired protein or regulatory sequence that modulate transcription of an existing sequence can be inserted.

Pigs that possess two inactive alleles of the alpha-1,3-GT gene are not naturally occurring. The predicted frequency of occurrence of such a pig would be in the range of $10^{-10}$ to $10^{-12}$, and has never been identified.

As one aspect of the invention, it was surprisingly discovered that while attempting to knockout the second allele of the alpha-1,3-GT gene through a genetic targeting event, a point mutation was identified, which rendered the second allele inactive. Pigs carrying point mutations in the alpha-1,3-GT gene are free of antibiotic-resistance genes and thus have the potential to make a safer product for human use. Thus, another aspect of the invention is a homozygous alpha-1,3-GT knock out that has no antibiotic resistant or other selectable marker genes. In one embodiment, this point mutation can occur via a genetic targeting event. In another embodiment, this point mutation can be naturally occurring.

In a further embodiment, mutations can be induced in the alpha-1,3-GT gene via a mutagenic agent.

In one specific embodiment the point mutation can be a T-to-G mutation at the second base of exon 9 of the alpha-1,3-GT gene (FIG. 2). In other embodiments, at least two, at least three, at least four, at least five, at least ten or at least twenty point mutations can exist to render the alpha-1,3-GT gene inactive. In other embodiments, pigs are provided in which both alleles of the alpha-1,3-GT gene contain point mutations that prevent any expression of functional alpha1,3GT. In a specific embodiment, pigs are provided that contain the T-to-G mutation at the second base of exon 9 in both alleles of the alpha-1,3-GT gene (FIG. 2).

Another aspect of the present invention provides a porcine animal, in which both alleles of the alpha-1,3-GT gene are inactivated, whereby one allele is inactivated by a genetic targeting event and the other allele is inactivated via a point mutation. In one embodiment, a porcine animal is provided, in which both alleles of the alpha-1,3-GT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the alpha-1,3-GT gene are inactivated, whereby one allele is inactivated via a targeting construct directed to Exon 9 (see, for example, FIG. 6) and the other allele is inactivated due to presence of a T-to-G point mutation at the second base of exon 9 (FIG. 2). Targeting, for example, can also be directed to exon 9, and or exons 4-8.

In a further embodiment, one allele is inactivated by a genetic targeting event and the other allele is inactivated due to presence of a T-to-G point mutation at the second base of exon 9 of the alpha-1,3-GT gene. In a specific embodiment, one allele is inactivated via a targeting construct directed to Exon 9 (see, for example, FIG. 6) and the other allele is inactivated due to presence of a T-to-G point mutation at the second base of exon 9 of the alpha-1,3-GT gene. In another embodiment, a method to clone such pigs includes: enucleating an oocyte, fusing the oocyte with a donor nucleus from a porcine cell that lacks expression of functional alpha1, 3GT, and implanting the nuclear transfer-derived embryo into a surrogate mother.

In another embodiment, the present invention provides a method for producing viable pigs that lack any expression of functional alpha-1,3-GT by breeding a male pig heterozygous for the alpha-1,3-GT gene with a female pig heterozygous for the alpha-1,3-GT gene. In one embodiment, the pigs are heterozygous due to the genetic modification of one allele of the alpha-1,3-GT gene to prevent expression of that allele. In another embodiment, the pigs are heterozygous due to the presence of a point mutation in one allele of the alpha-1,3-GT gene. In another embodiment, the point mutation can be a T-to-G point mutation at the second base of exon 9 of the alpha-1,3-GT gene. In one specific embodiment, a method to produce a porcine animal that lacks any expression of functional alpha-1,3-GT is provided wherein a male pig that contains a T-to-G point mutation at the second base of exon 9 of the alpha-1,3-GT gene is bred with a female pig that contains a T-to-G point mutation at the second base of exon 9 of the alpha-1,3-GT gene, or vise versa.

In another aspect of the present invention, a selection method is provided for determining whether porcine cells express galactose alpha1,3-galactose on the cell surface. In one embodiment, the selection procedure can be based on a bacterial toxin to select for cells that lack expression of galactose alpha1,3-galactose. In another embodiment, the bacterial toxin, toxin A produced by *Clostridium difficile*, can be used to select for such cells. Exposure to *C. difficile* toxin can cause rounding of cells that exhibit this epitope on their surface, releasing the cells from the plate matrix. Both targeted gene knockouts and mutations that disable enzyme function or expression can be detected using this selection method. Cells lacking cell surface expression of the galactose alpha 1,3-galactose, identified using Toxin A mediated selection described, or produced using standard methods of gene inactivation including gene targeting, can then be used to produce pigs that lack expression of functional alpha1, 3GT.

Other embodiments of the present invention will be apparent to one of ordinary skill in light of the following description of the invention, the claims and what is known in the art.

BRIEF DESCRIPTION OF THE DRAWINGS

FIG. 2 depicts a short segment of the coding region of the alpha-1,3-GT gene (see GenBank Acc. No. L36152) in which the point mutation selected by Toxin A occurs. Upper sequence occurs in wild type; lower sequence shows the change due to the point mutation in the second allele.

DETAILED DESCRIPTION OF THE INVENTION

Figure 1:
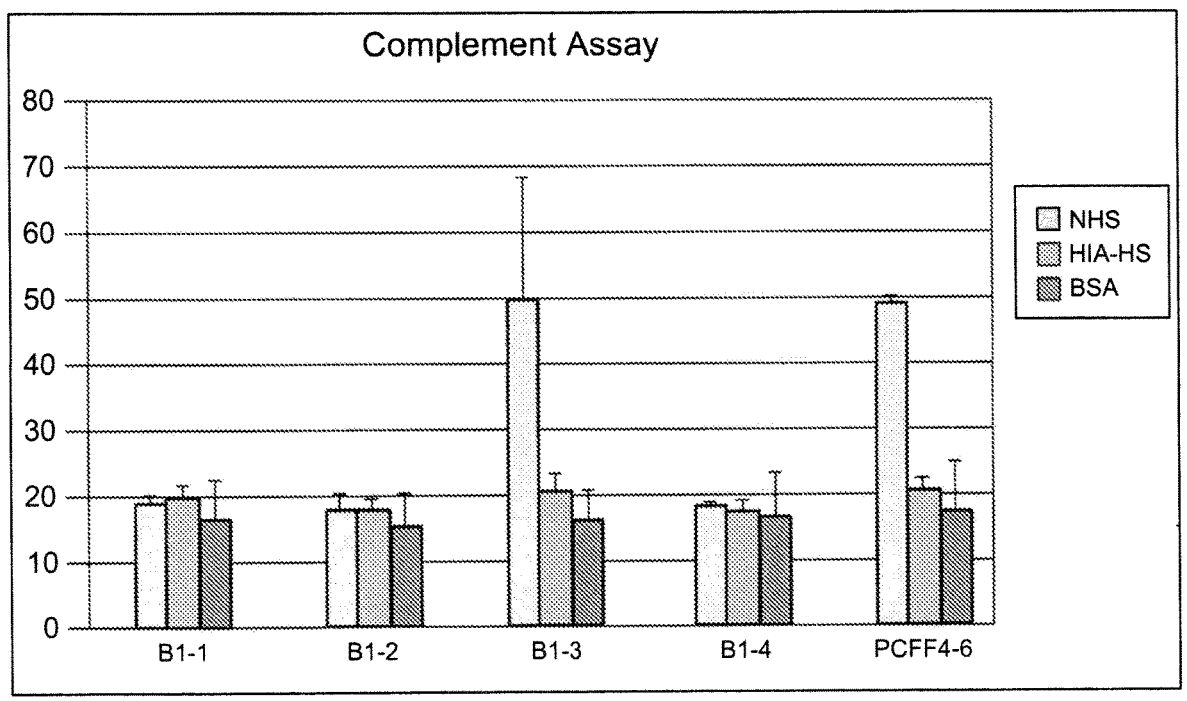
FIG. 1 is a graph depicting the relative lytic effects of complement on cells from fetuses 680B1-4.

We have now proven that a viable porcine animal that lacks any expression of functional alpha 1,3 galactosyltransferase can be produced. The present invention provides the complete inactivation of both alleles of the alpha 1,3 galactosyltransferase gene in pigs, thus overcoming this long-standing hurdle and making xenotransplantation a reality. Eliminating the expression of this gene, resulting in a lack of galactose alpha 1,3-galactose on the cell surface, represents the first and major step in eliminating hyperacute rejection in pig-to-human xenotransplantation therapy. The invention also provides organs, tissues, and cells derived from such porcine, which are useful for xenotransplantation.

In one aspect, the invention provides porcine organs, tissues and/or purified or substantially pure cells or cell lines obtained from pigs that lack any expression of functional alpha1,3GT. In another embodiment, the invention provides organs or tissues that are useful for xenotransplantation. In a further embodiment, the invention provides cells or cell lines that are useful for xenotransplantation.

Definitions

As used herein, the term "animal" (as in "genetically modified (or altered) animal") is meant to include any non-human animal, particularly any non-human mammal, including but not limited to pigs, sheep, goats, cattle (bovine), deer, mules, horses, monkeys, dogs, cats, rats, mice, birds, chickens, reptiles, fish, and insects. In one embodiment of the invention, genetically altered pigs and methods of production thereof are provided.

As used herein, an "organ" is an organized structure, which can be made up of one or more tissues. An "organ" performs one or more specific biological functions. Organs include, without limitation, heart, liver, kidney, pancreas, lung, thyroid, and skin.

As used herein, a "tissue" is an organized structure comprising cells and the intracellular substances surrounding them. The "tissue", alone or in conjunction with other cells or tissues can perform one or more biological functions.

As used herein, the terms "porcine", "porcine animal", "pig" and "swine" are generic terms referring to the same type of animal without regard to gender, size, or breed.

I. Genetic Targeting of the Alpha-1,3-GT Gene

In one aspect of the present invention, porcine animals are provided in which one allele of the alpha-1,3-GT gene is inactivated via a genetic targeting event. In another aspect of the present invention, porcine animals are provided in which both alleles of the alpha-1,3-GT gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knockout") or insertion ("knockin") techniques. Additional genes for a desired protein or regulatory sequence that modulate transcription of an existing sequence can be inserted.

In embodiments of the present invention, the alleles of the alpha-1,3-GT gene are rendered inactive, such that the resultant alpha-1,3-GT enzyme can no longer generate galactose alpha1,3-galactose on the cell surface. In one embodiment, the alpha-1,3-GT gene can be transcribed into RNA, but not translated into protein. In another embodiment, the alpha-1,3-GT gene can be transcribed in a truncated form. Such a truncated RNA can either not be translated or can be translated into a nonfunctional protein. In an alternative embodiment, the alpha-1,3-GT gene can be inactivated in such a way that no transcription of the gene occurs. In a further embodiment, the alpha-1,3-GT gene can be transcribed and then translated into a nonfunctional protein.

Pigs that possess two inactive alleles of the alpha-1,3-GT gene are not naturally occurring. It was surprisingly discovered that while attempting to knockout the second allele of the alpha-1,3-GT gene through a genetic targeting event, a point mutation was identified, which prevented the second allele from producing functional alpha1,3GT.

Thus, in another aspect of the present invention, the alpha-1,3-GT gene can be rendered inactive through at least one point mutation. In one embodiment, one allele of the alpha-1,3-GT gene can be rendered inactive through at least one point mutation. In another embodiment, both alleles of the alpha-1,3-GT gene can be rendered inactive through at least one point mutation. In one embodiment, this point mutation can occur via a genetic targeting event. In another embodiment, this point mutation can be naturally occurring. In a further embodiment, mutations can be induced in the alpha-1,3-GT gene via a mutagenic agent.

In one specific embodiment the point mutation can be a T-to-G mutation at the second base of exon 9 of the alpha-1,3-GT gene (FIG. 2). Pigs carrying a naturally occurring point mutation in the alpha-1,3-GT gene allow for the production of alpha1,3GT-deficient pigs free of antibiotic-resistance genes and thus have the potential to make a safer product for human use. In other embodiments, at least two, at least three, at least four, at least five, at least ten or at least twenty point mutations can exist to render the alpha-1,3-GT gene inactive. In other embodiments, pigs are provided in which both alleles of the alpha-1,3-GT gene contain point mutations that prevent any expression of functional alpha1, 3GT. In a specific embodiment, pigs are provided that contain the T-to-G mutation at the second base of exon 9 in both alleles of the alpha-1,3-GT gene (FIG. 2).

Another aspect of the present invention provides a porcine animal, in which both alleles of the alpha-1,3-GT gene are inactivated, whereby one allele is inactivated by a genetic targeting event and the other allele is inactivated via a mutation. In one embodiment, a porcine animal is provided, in which both alleles of the alpha-1,3-GT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the alpha-1,3-GT gene are inactivated, whereby one allele is inactivated via a targeting construct directed to Exon 9 (see, for example, FIG. 6) and the other allele is inactivated due to presence of a T-to-G point mutation at the second base of exon 9.

Types of Porcine Cells

Porcine cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, porcine cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts.

In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF). In a preferred embodiment, the porcine cells can be fibroblasts; in one specific embodiment, the porcine cells can be fetal fibroblasts. Fibroblast cells are a preferred somatic cell type because they can be obtained from developing fetuses and adult animals in large quantities. These cells can be easily propagated in vitro with a rapid doubling time and can be clonally propagated for use in gene targeting procedures.

Targeting Constructs

Homologous Recombination

Homologous recombination permits site-specific modifications in endogenous genes and thus novel alterations can be engineered into the genome. In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells. Illustrative of these papers are Kucherlapati et al., Proc. Natl. Acad. Sci. USA 81:3153-3157, 1984; Kucherlapati et al., Mol. Cell. Bio. 5:714-720, 1985; Smithies et al, Nature 317:230-234, 1985; Wake et al., Mol. Cell. Bio. 8:2080-2089, 1985; Ayares et al., Genetics 111:375-388, 1985; Ayares et al., Mol. Cell. Bio. 7:1656-1662, 1986; Song et al., Proc. Natl. Acad. Sci. USA 84:6820-6824, 1987; Thomas et al. Cell 44:419-428, 1986; Thomas and Capecchi, Cell 51: 503-512, 1987; Nandi et al., Proc. Natl. Acad. Sci. USA 85:3845-3849, 1988; and Mansour et al., Nature 336:348-352, 1988. Evans and Kaufman, Nature 294:146-154, 1981; Doetschman et al., Nature 330: 576-578, 1987; Thoma and Capecchi, Cell 51:503-512, 4987; Thompson et al., Cell 56:316-321, 1989.

The present invention uses homologous recombination to inactivate the alpha-1,3-GT gene in cells, such as the porcine cells described above. The DNA can comprise at least a portion of the gene(s) at the particular locus with introduction of an alteration into at least one, optionally both copies, of the native gene(s), so as to prevent expression of functional alpha1,3GT. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Targeting Vectors

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424, FIG. 6.

Various constructs can be prepared for homologous recombination at a target locus. The construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of the porcine alpha-1,3-GT gene (see, for example, GenBank Acc. No. L36152, WO0130992 to The University of Pittsburgh of the Commonwealth System of Higher Education; WO 01/123541 to Alexion, Inc.).

Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The DNA constructs can be designed to modify the endogenous, target alpha1,3GT. The homologous sequence for targeting the construct can have one or more deletions, insertions, substitutions or combinations thereof. The alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See, for example, Song, K-Y., et al. Proc. Nat'l Acad. Sci. U.S.A. 84:6820-6824 (1987); Sambrook, J., et al., Molecular Cloning—A Laboratory Manual, Cold Spring Harbor Laboratory, Cold Spring Harbor, N.Y. (1989), Chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, J. Mol. Appl. Genet. 1:327-341 (1982)); and the hygromycin resistance gene (hyg) (Nucleic Acids Research 11:6895-6911 (1983), and Te Riele, H., et al., Nature 348:649-651 (1990)). Other selectable marker genes include: acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. Nos. 6,080,576; 6,136,566; Niwa et al., J. Biochem. 113: 343-349 (1993); and Yoshida et al., Transgenic Research 4:277-287 (1995)).

TABLE 1

Selectable marker genes that emit detectable signals

| U.S. Pat. No. | Title |
|---|---|
| 6,319,669 | Modified green fluorescent proteins |
| 6,316,181 | Establishment of cell lines with persistent expression of a green fluorescent protein (GFP) using a pIRES/EGFP DNA vector construct |
| 6,303,373 | Method of measuring plasma membrane targeting of GLUT4 |
| 6,291,177 | Assay for agents which alter G-protein coupled receptor activity |
| 6,284,519 | Cell systems having specific interaction of peptide binding pairs |
| 6,284,496 | DNA vector for determining the presence of out-of-reading-frame mutations |
| 6,280,934 | Assay for agents which alter G-protein coupled receptor activity |
| 6,274,354 | Methods using cre-lox for production of recombinant adeno-associated viruses |
| 6,270,958 | Detection of negative-strand RNA viruses |
| 6,268,201 | IniB, iniA and iniC genes of mycobacteria and methods of use |
| 6,265,548 | Mutant Aequorea victoria fluorescent proteins having increased cellular fluorescence |
| 6,261,760 | Regulation of the cell cycle by sterols |
| 6,255,558 | Gene expression |
| 6,255,071 | Mammalian viral vectors and their uses |
| 6,251,677 | Hybrid adenovirus-AAV virus and methods of use thereof |
| 6,251,602 | Cell systems having specific interaction of peptide binding pairs |
| 6,251,582 | Alternative G-coupled receptors associated with retroviral entry into cells, methods of identifying the same and diagnostic and therapeutic uses thereof |
| 6,251,384 | Metastasis models using green fluorescent protein (GFP) as a marker |
| 6,248,558 | Sequence and method for genetic engineering of proteins with cell membrane translocating activity |
| 6,248,550 | Assays for protein kinases using fluorescent protein substrates |
| 6,248,543 | Compositions and methods for screening antimicrobials |
| 6,232,107 | Luciferases, fluorescent proteins, nucleic acids encoding the luciferases and fluorescent proteins and the use thereof in diagnostics, high throughput screening and novelty items |
| 6,228,639 | Vectors and methods for the mutagenesis of mammalian genes |
| 6,225,082 | Myelin basic protein MRNA transport and translation enhancer sequences |
| 6,221,612 | Photon reducing agents for use in fluorescence assays |
| 6,218,185 | Piggybac transposon-based genetic transformation system for insects |
| 6,214,567 | Immortalized human keratinocyte cell line |
| 6,214,563 | Photon reducing agents for reducing undesired light emission in assays |
| 6,210,922 | Serum free production of recombinant proteins and adenoviral vectors |
| 6,210,910 | Optical fiber biosensor array comprising cell populations confined to microcavities |
| 6,203,986 | Visualization of RNA in living cells |
| 6,197,928 | Fluorescent protein sensors for detection of analytes |
| 6,180,343 | Green fluorescent protein fusions with random peptides |
| 6,172,188 | Fluorescent proteins |
| 6,153,409 | Process for continuous optimized protein production in insect larvae |
| 6,150,176 | Fluorescent protein sensors for measuring the pH of a biological sample |
| 6,146,826 | Green fluorescent protein |
| 6,140,132 | Fluorescent protein sensors for measuring the pH of a biological sample |
| 6,136,539 | Compositions and methods for the inhibition of MUC-5 mucin gene expression |
| 6,136,538 | Silent inducible virus replicons and uses thereof |
| 6,133,429 | Chromophores useful for the preparation of novel tandem conjugates |
| 6,130,313 | Rapidly degrading GFP-fusion proteins |
| 6,124,128 | Long wavelength engineered fluorescent proteins |

TABLE 1-continued

Selectable marker genes that emit detectable signals

| U.S. Pat. No. | Title |
|---|---|
| 6,110,711 | Method of defining cell types by probing comprehensive expression libraries with amplified RNA |
| 6,096,865 | Mutants of the green fluorescent protein having improved fluorescent properties at 37 degrees |
| 6,096,717 | Method for producing tagged genes transcripts and proteins |
| 6,093,808 | IκB eGFP constructs, cell lines and methods of use |
| 6,090,919 | FACS-optimized mutants of the green fluorescent protein (GFP) |
| 6,083,690 | Methods and compositions for identifying osteogenic agents |
| 6,077,707 | Long wavelength engineered fluorescent proteins |
| 6,066,476 | Modified green fluorescent proteins |
| 6,060,247 | Post-mitotic neurons containing adenovirus vectors that modulate apoptosis and growth |
| 6,054,321 | Long wavelength engineered fluorescent proteins |
| 6,037,133 | IκB eGFP constructs, cell lines and methods of use |
| 6,027,881 | Mutant *Aequorea victoria* fluorescent proteins having increased cellular fluorescence |
| 6,025,192 | Modified retroviral vectors |
| 6,020,192 | Humanized green fluorescent protein genes and methods |
| 6,013,447 | Random intracellular method for obtaining optimally active nucleic acid molecules |
| 6,001,557 | Adenovirus and methods of use thereof |
| 5,994,077 | Fluorescence-based isolation of differentially induced genes |
| 5,994,071 | Assessment of prostate cancer |
| 5,993,778 | Functional expression of, and assay for, functional cellular receptors in vivo |
| 5,989,808 | Identification of compounds affecting specific interaction of peptide binding pairs |
| 5,985,577 | Protein conjugates containing multimers of green fluorescent protein |
| 5,968,773 | System and method for regulation of gene expression |
| 5,968,738 | Two-reporter FACS analysis of mammalian cells using green fluorescent proteins |
| 5,958,713 | Method of detecting biologically active substances by using green fluorescent protein |
| 5,952,236 | Enzyme-based fluorescence biosensor for chemical analysis |
| 5,948,889 | Compositions and methods for screening antimicrobials |
| 5,948,681 | Non-viral vehicles for use in gene transfer |
| 5,942,387 | Combinatorial process for preparing substituted thiophene libraries |
| 5,932,435 | Screening antisense and ribozyme nucleic acids in *schizosaccharomyces pombe* |
| 5,922,576 | Simplified system for generating recombinant adenoviruses |
| 5,919,445 | Use of green fluorescent protein to trace the infection of baculovirus in insects and to increase viral UV stability |
| 5,914,233 | Screening assay for the identification of agents which alter expression of PTH-rP |

Combinations of selectable markers can also be used. For example, to target alpha1,3GT, a neo gene (with or without its own promoter, as discussed above) can be cloned into a DNA sequence which is homologous to the alpha-1,3-GT gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the alpha-1,3-GT gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. The mutation can be a subtle change, not exceeding about 5% of the homologous flanking sequences. Where mutation of a gene is desired, the marker gene can be inserted into an intron or an exon.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

The present invention further includes recombinant constructs containing sequences of the alpha-1,3-GT gene. The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia), viral origin vectors (M13 vectors, bacterial phage 1 vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8). Other vectors include prokaryotic expression vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99 A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof. Additional vectors that can be used include: pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSVSPORT1 (Invitrogen), pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZa, pGAPZ, pGAPZa, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP10, pCEP4, pEBVHis, pCR3.1, pCR2.1, pCR3.1-Uni, and pCRBac from Invitrogen; λExCell, λgt11, pTrc99A, pKK223-3, pGEX-10T, pGEX-2T, pGEX-2TK, pGEX-4T-1, pGEX-4T-2, pGEX-4T-3, pGEX-3X, pGEX-5x-1, pGEX-5x-2, pGEX-5x-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b (+), pET-21abcd(+), pET-22b(+), pET-23abcd(+), pET-24abcd(+), pET-25 b(+), pET-26b(+), pET-27b(+), pET-28 abc(+), pET-29abc(+), pET-30 abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6×His-GFP, pSEAP2-Basic, pSEAP2-Contral, pSEAP2-Promoter, pSEAP2-Enhancer, pβgal-Basic, pβgal-Control, pβgal-Promoter, βgal-Enhancer, pCMVβ, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Script Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene and variants or derivatives thereof. Two-hybrid and reverse two-hybrid vectors can also be used, for example, pPC86, pDBLeu, pDBTrp, pPC97, p2.5, pGADI-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof. Any other plasmids and vectors may be used as long as they are replicable and viable in the host.

Techniques which can be used to allow the DNA construct entry into the host cell include calcium phosphate/DNA co precipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., Methods in Enzymology Vol. 185, pp. 527-537 (1990).

In one specific embodiment, heterozygous knockout cells can be produced by transfection of primary porcine fetal fibroblasts with a knockout vector containing alpha-1,3-GT sequence isolated from isogenic DNA. As described in Dai et al. (Nature Biotechnology, 20:451-455), the 5' arm can be 4.9 kb and be comprised of a large fragment of intron 8 and the 5' end of exon 9. The 3' arm can be and be comprised of exon 9 sequence. The vector can incorporate a promoter trap strategy, using, for example, IRES (internal ribosome entry site) to initiate translation of the Neor gene (see, for example, FIG. 6).

Selection of Homologously Recombined Cells

The cells can then be grown in appropriately-selected medium to identify cells providing the appropriate integration. The presence of the selectable marker gene inserted into the alpha-1,3-GT gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the alpha-1,3-GT gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

Induced Mutation in the Alpha 1,3 GT Locus

In certain other embodiments, the methods of the invention involve the intentional introduction of a mutation via a mutagenic agent. Examples of mutagenic agents known in the art and suitable for use in the present invention include, but are not limited to, chemical mutagens (e.g., DNA-intercalating or DNA-binding chemicals such as N-ethyl-N-nitrosourea (ENU), ethylmethanesulphonate (EMS), mustard gas, ICR191 and the like; see, e.g., E. C. Friedberg, G. C. Walker, W. Siede, DNA Repair and Mutagenesis, ASM Press, Washington D.C. (1995), physical mutagens (e.g., UV radiation, radiation, x-rays), biochemical mutagens (e.g., restriction enzymes, DNA repair mutagens, DNA repair inhibitors, and error-prone DNA polymerases and replication proteins), as well as transposon insertion. According to the methods of the present invention, cells in culture can be exposed to one of these agents, and any mutation resulting in the depletion of galactose alpha1,3-galactose on the cell surface can be selected, for example, via exposure to toxin A.

Preferred doses of chemical mutagens for inducing mutations in cells are known in the art, or can be readily determined by the ordinarily skilled artisan using assays of mutagenesis known in the art. Chemical mutagenesis of cells in vitro can be achieved by treating the cells with various doses of the mutagenic agent and/or controlling the time of exposure to the agent. By titrating the mutagenic agent exposure and/or dose, it is possible to carry out the optimal degree of mutagenesis for the intended purpose, thereby mutating a desired number of genes in each target cell. For example, useful doses of ENU can be 0.1-0.4 mg/ml for approximately 1-2 hours. In another example, useful doses of EMS can be 0.1-1 mg/ml for approximately 10-30 hours. In addition, lower and higher doses and exposure times can also be used to achieve the desired mutation frequency.

II. Identification of Cells that do not Express Functional Alpha-1,3-GT

In another aspect of the present invention, a selection method is provided for determining whether porcine cells lack expression of functional alpha-1,3-GT.

In one embodiment, the selection procedure can be based on a bacterial toxin to select for cells that lack expression of functional alpha1,3GT. In another embodiment, the bacterial toxin, toxin A produced by *Clostridium difficile*, can be used to select for cells lacking the cell surface epitope galactose alpha1,3-galactose. Exposure to *C. difficile* toxin can cause rounding of cells that exhibit this epitope on their surface, releasing the cells from the plate matrix. Both targeted gene knockouts and mutations that disable enzyme function or expression can be detected using this selection method. Cells lacking cell surface expression of the galactose alpha 1,3-galactose epitope, identified using Toxin A mediated selection described, or produced using standard methods of gene inactivation including gene targeting, can then be used to produce pigs, in which both alleles of the alpha 1,3 GT gene are inactive.

In one embodiment, the selection method can detect the depletion of the alpha 1,3GT epitope directly, whether due to targeted knockout of the alpha 1,3GT gene by homologous recombination, or a mutation in the gene that results in a nonfunctioning or nonexpressed enzyme. Selection via antibiotic resistance has been used most commonly for screening (see above). This method can detect the presence of the resistance gene on the targeting vector, but does not directly indicate whether integration was a targeted recombination event or a random integration. Certain technology, such as Poly A and promoter trap technology, increase the probability of targeted events, but again, do not give direct evidence that the desired phenotype, a cell deficient in gal alpha 1.3 gal epitopes on the cell surface, has been achieved. In addition, negative forms of selection can be used to select for targeted integration; in these cases, the gene for a factor lethal to the cells is inserted in such a way that only targeted events allow the cell to avoid death. Cells selected by these methods can then be assayed for gene disruption, vector integration and, finally, alpha 1,3gal epitope depletion. In these cases, since the selection is based on detection of targeting vector integration and not at the altered phenotype, only targeted knockouts, not point mutations, gene rearrangements or truncations or other such modifications can be detected.

Toxin A, a cytotoxin produced by the bacterium *Clostridium difficile*, specifically binds the terminal carbohydrate galactose alpha1,3-galactose sequence gal alpha 1-3gal beta 1-4GlcNAc. Binding to this receptor mediates a cytotoxic effect on the cell, causing it to change morphology and, in some cases, to release from the plate matrix. Under controlled conditions, cells not carrying this marker are unaffected by the toxin. Thus, in one embodiment, to determine whether or not the alpha 1.3 gal epitope has been successfully eliminated via targeted knockout or gene mutation of the gal alpha-1,3-GT locus, cells that do not carry the epitope can be selected. Exposure to toxin A can be toxic for cells carrying the epitope, and promote selection for those cells in which the gene has been successfully inactivated. Thus, according to on aspect of the present invention, cells useful as nuclear donors for production of genetically altered animals (e.g., pigs) that are knocked out or mutated in the gal alpha 1,3 locus are selected by exposure of cells to *C. difficile* toxin A.

Toxin A, one of two cytotoxins produced by *Clostridium difficile*, has a high binding affinity for the galactose alpha1, 3-galactose sequence gal alpha 1,3-gal beta 1,4GlcNAc found on the surface of a variety of cell types (Clark et al., Arch. Biochem. Biophys. 257 (1): 217-229, 1987). This carbohydrate seems to serve as a functional receptor for Toxin A, as cells displaying this epitope on their surface are more sensitive to the cytotoxic effect of toxin A than are cells lacking this receptor. Sensitive cells exposed to toxin A in culture exhibit cell rounding, probably due to actin depolymerization and resultant changes in cytoskeletal integrity (Kushnaryov et al., J. Biol. Chem. 263: 17755-17762 (1988) and Just et al., J. Clin. Invest. 95: 1026-1031,1995). These cells can be selectively removed from the culture, as they lift from the matrix and float in suspension, leaving unaffected cells firmly attached to the plate surface.

Exposure of cells to toxin A. In one embodiment, attached cells are exposed to toxin A as a component of cell culture media. After a fixed time of exposure, the media containing the toxin A and released toxin A-sensitive cells are removed, the plate washed, and the media, without toxin A, replenished. The exposure to toxin A is repeated over a period of days to remove attached toxin-sensitive cells from the plates, and allow insensitive cells to proliferate and expand. Purified toxin A can be used in the methods of the present invention (available commercially, see for example, Techlab Inc., Cat. #T3001, Blacksburg, Va.). Crude unpurified toxin A can also be used (available commercially, see for example, Techlab Inc. Cat. #T5000 or T3000, Blacksburg, Va.), which can require initial titering to determine effective dosage for selection.

Serum Based Selection Method

In another embodiment, the selection procedure can be conducted using serum containing complement factors and natural antibodies to the gal alpha1,3gal epitope (see, for example, Koike et al., Xenotransplantation 4:147-153, 1997). Exposure to serum from a human or non-human primate that contains anti-Gal antibodies can cause cell lysis due to specific antibody binding and complement activation in cells that exhibit gal alpha 1.3 gal epitope. Therefore, cells deficient in alpha-1,3-GT will remain alive and thus can be selected.

Further Characterization of Porcine Cells Lacking Expression of Functional alpha1,3GT Porcine cells believed to lacking expression of functional alpha-1,3-GT can be further characterized. Such characterization can be accomplished by the following techniques, including, but not limited to: PCR analysis, Southern blot analysis, Northern blot analysis, specific lectin binding assays, and/or sequencing analysis.

PCR analysis as described in the art (see, for example, Dai et al. Nature Biotechnology 20:431-455) can be used to determine the integration of targeting vectors. In one embodiment, amplimers can originate in the antibiotic resistance gene and extend into a region outside the vector sequence. Southern analysis (see, for example, Dai et al. Nature Biotechnology 20:431-455) can also be used to characterize gross modifications in the locus, such as the integration of a targeting vector into the alpha 1,3GT locus. Whereas, Northern analysis can be used to characterize the transcript produced from each of the alleles.

Specific lectin binding, using GSL IB4 lectin from Griffonia (Bandeiraea) simplicifolia (Vector Labs), a lectin that specifically binds the carbohydrate moiety gal alpha 1.3 gal, and FACS (fluorescent antibody cell sorting) analysis of binding can determine whether or not the alpha 1.3 gal epitope is present on the cells. This type of analysis involves the addition of fluorescein-labeled GSL-IB4 lectin to the cells and subsequent cell sorting.

Further, sequencing analysis of the cDNA produced from the RNA transcript can also be used to determine the precise location of any mutations in the alpha 1,3GT allele.

III. Production of Porcine Animals

In yet another aspect, the present invention provides a method for producing viable pigs in which both alleles of the alpha-1,3-GT gene have been rendered inactive. In one embodiment, the pigs are produced by cloning using a donor nucleus from a porcine cell in which both alleles of the alpha-1,3-GT gene have been inactivated. In one embodiment, both alleles of the alpha-1,3-GT gene are inactivated via a genetic targeting event. In another embodiment, both alleles of the alpha-1,3-GT gene are inactivated due to the presence of a point mutation. In another embodiment, one allele is inactivated by a genetic targeting event and the other allele is inactivated via a point mutation. In a further embodiment, one allele is inactivated by a genetic targeting event and the other allele is inactivated due to presence of a T-to-G point mutation at the second base of exon 9 of the alpha-1,3-GT gene. In a specific embodiment, one allele is inactivated via a targeting construct directed to Exon 9 (FIG. 6) and the other allele is inactivated due to presence of a T-to-G point mutation at the second base of exon 9 of the alpha-1,3-GT gene. In another embodiment, a method to clone such pigs includes: enucleating an oocyte, fusing the oocyte with a donor nucleus from a porcine cell in which both alleles of the alpha-1,3-GT gene have been inactivated, and implanting the nuclear transfer-derived embryo into a surrogate mother.

Alternatively, a method is provided for producing viable pigs that lack any expression of functional alpha-1,3-GT by inactivating both alleles of the alpha-1,3-GT gene in embryonic stem cells, which can then be used to produce offspring.

Genetically altered animals that can be created by modifying zygotes directly. For mammals, the modified zygotes can be then introduced into the uterus of a pseudopregnant female capable of carrying the animal to term. For example, if whole animals lacking the alpha-1,3-GT gene are desired, then embryonic stem cells derived from that animal can be targeted and later introduced into blastocysts for growing the modified cells into chimeric animals. For embryonic stem cells, either an embryonic stem cell line or freshly obtained stem cells can be used.

In a suitable embodiment of the invention, the totipotent cells are embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang et al., Nature 336:741-744 (1992). In another suitable embodiment of the invention, the totipotent cells are embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui et al., Cell 70:841-847 (1992); Resnick et al., Nature 359: 550-551 (1992)). The cultivation of EG cells can be carried out using methods described in the article by Donovan et al., "Transgenic Animals, Generation and Use," Ed. L. M. Houdebine, Harwood Academic Publishers (1997), and in the original literature cited therein.

Tetraploid blastocysts for use in the invention may be obtained by natural zygote production and development, or by known methods by electrofusion of two-cell embryos and subsequently cultured as described, for example, by James et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art. A suitable method for the purposes of the present invention is the microinjection method as described by Wang et al., EMBO J. 10:2437-2450 (1991).

Alternatively, by modified embryonic stem cells transgenic animals can be produced. The genetically modified embryonic stem cells can be injected into a blastocyst and then brought to term in a female host mammal in accordance with conventional techniques. Heterozygous progeny can then be screened for the presence of the alteration at the site of the target locus, using techniques such as PCR or Southern blotting. After mating with a wild-type host of the same species, the resulting chimeric progeny can then be crossmated to achieve homozygous hosts.

After transforming embryonic stem cells with the targeting vector to alter the alpha-1,3-GT gene, the cells can be plated onto a feeder layer in an appropriate medium, e.g., fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified alpha-1,3-GT gene.

Somatic Cell Nuclear Transfer to Produce Cloned, Transgenic Offspring

The present invention provides a method for cloning a pig lacking a functional alpha-1,3-GT gene via somatic cell nuclear transfer. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form NT units; activating the resultant NT unit; and transferring said cultured NT unit to a host pig such that the NT unit develops into a fetus.

Nuclear transfer techniques or nuclear transplantation techniques are known in the art (Dai et al. Nature Biotechnology 20:251-255; Polejaeva et al Nature 407:86-90 (2000); Campbell et al, Theriogenology, 43:181 (1995); Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, U.S. Pat. Nos. 4,944,384 and 5,057,420).

A donor cell nucleus, which has been modified to alter the alpha-1,3-GT gene, is transferred to a recipient porcine oocyte. The use of this method is not restricted to a particular donor cell type. The donor cell can be as described herein, see also, for example, Wilmut et al Nature 385 810 (1997); Campbell et al Nature 380 64-66 (1996); Dai et al., Nature Biotechnology 20:251-255, 2002 or Cibelli et al Science 280 1256-1258 (1998). All cells of normal karyotype, including embryonic, fetal and adult somatic cells which can be used successfully in nuclear transfer can be employed. Fetal fibroblasts are a particularly useful class of donor cells. Generally suitable methods of nuclear transfer are described in Campbell et al Theriogenology 43 181 (1995), Dai et al. Nature Biotechnology 20:251-255, Polejaeva et al Nature 407:86-90 (2000), Collas et al Mol. Reprod. Dev. 38 264-267 (1994), Keefer et al Biol. Reprod. 50 935-939 (1994), Sims et al Proc. Nat'l. Acad. Sci. USA 90 6143-6147 (1993), WO-A-9426884, WO-A-9424274, WO-A-9807841, WO-A-9003432, U.S. Pat. Nos. 4,994,384 and 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell et al (Nature, 380:64-68, 1996) and Stice et al (Biol. Reprod., 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells or endothelial cells. In another embodiment, the nuclear donor cell is an embryonic stem cell. In a preferred embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (G0, G1, G2, S, M) so as to ensure coordination with the acceptor cell. Any method known in the art may be used to manipulate the cell cycle phase. Methods to control the cell cycle phase include, but are not limited to, G0 quiescence induced by contact inhibition of cultured cells, G0 quiescence induced by removal of serum or other essential nutrient, G0 quiescence induced by senescence, G0 quiescence induced by addition of a specific growth factor; G0 or G1 quiescence induced by physical or chemical means such as heat shock, hyperbaric pressure or other treatment with a chemical, hormone, growth factor or other substance; S-phase control via treatment with a chemical agent which interferes with any point of the replication procedure; M-phase control via selection using fluorescence activated cell sorting, mitotic shake off, treatment with microtubule disrupting agents or any chemical which disrupts progression in mitosis (see also Freshney, R. I., "Culture of Animal Cells: A Manual of Basic Technique," Alan R. Liss, Inc, New York (1983).

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period". In certain embodiments, the oocyte is obtained from a gilt. A "gilt" is a female pig that has never had offspring. In other embodiments, the oocyte is obtained from a sow. A "sow" is a female pig that has previously produced offspring.

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, which ranges from about 10 to 40 hours, and preferably about 16-18 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, preferably not more than 24 hours later, and more preferably 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, Mol. Reprod. Dev., 38:264-267 (1994). After fusion, the resultant fused NT units are then placed in a suitable medium until activation, for example, CR1aa medium. Typically activation can be effected shortly thereafter, for example less than 24 hours later, or about 4-9 hours later, or optimally 1-2 hours after fusion. In a preferred embodiments, activation occurs at least one hour post fusion and at 40-41 hours post maturation.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720, to Susko-Parrish et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units, or "fused embryos", can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+ 10% fetal calf serum, Tyrodes-Albumin-Lactate-Pyruvate (TALP), Dulbecco's Phosphate Buffered Saline (PBS), Eagle's and Whitten's media, and, in one specific example, the activated NT units can be cultured in NCSU-23 medium for about 1-4 h at approximately 38.6° C. in a humidified atmosphere of 5% CO2.

Afterward, the cultured NT unit or units can be washed and then placed in a suitable media contained in well plates which preferably contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. Preferably, these NT units can be cultured until at least about 2 to 400 cells, about 4 to 128 cells, or at least about 50 cells.

Activated NT units can then be transferred (embryo transfers) to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg Regu-Mate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers of the can then be performed about 22-26 h after the hCG injection. In one embodiment, the pregnancy can be brought to term and result in the birth of live offspring. In another embodiment, the pregnancy can be terminated early and embryonic cells can be harvested.

Breeding for Desired Homozygous Knockout Animals

In another aspect, the present invention provides a method for producing viable pigs that lack any expression of functional alpha-1,3-GT is provided by breeding a male pig heterozygous for the alpha-1,3-GT gene with a female pig heterozygous for the alpha-1,3-GT gene. In one embodiment, the pigs are heterozygous due to the genetic modification of one allele of the alpha-1,3-GT gene to prevent expression of that allele. In another embodiment, the pigs are heterozygous due to the presence of a point mutation in one allele of the alpha-1,3-GT gene. In another embodiment, the point mutation can be a T-to-G point mutation at the second base of exon 9 of the alpha-1,3-GT gene. In one specific embodiment, a method to produce a porcine animal that lacks any expression of functional alpha-1,3-GT is provided wherein a male pig that contains a T-to-G point mutation at the second base of exon 9 of the alpha-1,3-GT gene is bred with a female pig that contains a T-to-G point mutation at the second base of exon 9 of the alpha-1,3-GT gene.

In one embodiment, sexually mature animals produced from nuclear transfer from donor cells that carrying a double knockout in the alpha-1,3-GT gene, can be bred and their offspring tested for the homozygous knockout. These homozygous knockout animals can then be bred to produce more animals.

In another embodiment, oocytes from a sexually mature double knockout animal can be in vitro fertilized using wild type sperm from two genetically diverse pig lines and the embryos implanted into suitable surrogates. Offspring from these matings can be tested for the presence of the knockout, for example, they can be tested by cDNA sequencing, PCR, toxin A sensitivity and/or lectin binding. Then, at sexual maturity, animals from each of these litters can be mated.

In certain methods according to this aspect of the invention, pregnancies can be terminated early so that fetal fibroblasts can be isolated and further characterized phenotypically and/or genotypically. Fibroblasts that lack expression of the alpha-1,3-GT gene can then be used for nuclear transfer according to the methods described herein (see also Dai et al.) to produce multiple pregnancies and offspring carrying the desired double knockout.

IV. Types of Genetically Modified Porcine Animals

In one aspect of the present invention, porcine animals are provided in which one allele of the alpha-1,3-GT gene is inactivated via a genetic targeting event. In another aspect of the present invention, porcine animals are provided in which both alleles of the alpha-1,3-GT gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knockout") or insertion ("knockin") techniques. Additional genes for a desired protein or regulatory sequence that modulate transcription of an existing sequence can be inserted.

Pigs that possess two inactive alleles of the alpha-1,3-GT gene are not naturally occurring. It was surprisingly discovered that while attempting to knockout the second allele of the alpha-1,3-GT gene through a genetic targeting event, a point mutation was identified, which rendered the second allele inactive.

Thus, in another aspect of the present invention, the alpha-1,3-GT gene can be rendered inactive through at least one point mutation. In one embodiment, one allele of the alpha-1,3-GT gene can be rendered inactive through at least one point mutation. In another embodiment, both alleles of the alpha-1,3-GT gene can be rendered inactive through at least one point mutation. In one embodiment, this point mutation can occur via a genetic targeting event. In another embodiment, this point mutation can be naturally occurring. In one specific embodiment the point mutation can be a T-to-G mutation at the second base of exon 9 of the alpha-1,3-GT gene (FIG. 2). Pigs carrying a naturally occurring point mutation in the alpha-1,3-GT gene allow for the production of alpha1,3GT-deficient pigs free of antibiotic-resistance genes and thus have the potential to make a safer product for human use. In other embodiments, at least two, at least three, at least four, at least five, at least ten or at least twenty point mutations can exist to render the alpha-1,3-GT gene inactive. In other embodiments, pigs are provided in which both alleles of the alpha-1,3-GT gene contain point mutations that prevent any expression of functional alpha1, 3GT. In a specific embodiment, pigs are provided that contain the T-to-G mutation at the second base of exon 9 in both alleles of the alpha-1,3-GT gene (FIG. 2).

Another aspect of the present invention provides a porcine animal, in which both alleles of the alpha-1,3-GT gene are inactivated, whereby one allele is inactivated by a genetic targeting event and the other allele is inactivated via a naturally occurring point mutation. In one embodiment, a porcine animal is provided, in which both alleles of the alpha-1,3-GT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the alpha-1,3-GT gene are inactivated, whereby one allele is inactivated via a targeting construct directed to Exon 9 (FIG. 6) and the other allele is inactivated due to presence of a T-to-G point mutation at the second base of exon 9.

V. Porcine Organs, Tissues, Cells and Cell Lines

The present invention provides, for the first time, viable porcine in which both alleles of the alpha 1,3 galactosyltransferase gene have been inactivated. The invention also provides organs, tissues, and cells derived from such porcine, which are useful for xenotransplantation.

In one embodiment, the invention provides porcine organs, tissues and/or purified or substantially pure cells or cell lines obtained from pigs that lack any expression of functional alpha1,3GT.

In one embodiment, the invention provides organs that are useful for xenotransplantation. Any porcine organ can be used, including, but not limited to: brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels.

In another embodiment, the invention provides tissues that are useful for xenotransplantation. Any porcine tissue can be used, including, but not limited to: epithelium, connective tissue, blood, bone, cartilage, muscle, nerve, adenoid, adipose, areolar, bone, brown adipose, cancellous, muscle, cartaginous, cavernous, chondroid, chromaffin, dartoic, elastic, epithelial, fatty, fibrohyaline, fibrous, Gamgee, gelatinous, granulation, gut-associated lymphoid, Haller's vascular, hard hemopoietic, indifferent, interstitial, investing, islet, lymphatic, lymphoid, mesenchymal, mesonephric, mucous connective, multilocular adipose, myeloid, nasion soft, nephrogenic, nodal, osseous, osteogenic, osteoid, periapical, reticular, retiform, rubber, skeletal muscle, smooth muscle, and subcutaneous tissue.

In a further embodiment, the invention provides cells and cell lines from porcine animals that lack expression of functional alpha1,3GT. In one embodiment, these cells or cell lines can be used for xenotransplantation. Cells from any porcine tissue or organ can be used, including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, pancreatic insulin secreting cells, pancreatic alpha-2 cells, pancreatic beta cells, pancreatic alpha-1 cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopaminergic cells, squamous epithelial cells, osteocytes, osteoblasts, osteoclasts, dopaminergic cells, embryonic stem cells, fibroblasts and fetal fibroblasts. In a specific embodiment, pancreatic cells, including, but not limited to, Islets of Langerhans cells, insulin secreting cells, alpha-2 cells, beta cells, alpha-1 cells from pigs that lack expression of functional alpha-1,3-GT are provided.

Nonviable derivatives include tissues stripped of viable cells by enzymatic or chemical treatment these tissue derivatives can be further processed via crosslinking or other chemical treatments prior to use in transplantation. In a preferred embodiment, the derivatives include extracellular matrix derived from a variety of tissues, including skin, urinary, bladder or organ submucosal tissues. Also, tendons, joints and bones stripped of viable tissue to include heart valves and other nonviable tissues as medical devices are provided.

Therapeutic Uses

The cells can be administered into a host in order in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type I, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antitrypsin deficiency, etc.

Diseases or pathologies include neurodegenerative diseases, hepatodegenerative diseases, nephrodegenerative disease, spinal cord injury, head trauma or surgery, viral infections that result in tissue, organ, or gland degeneration, and the like. Such neurodegenerative diseases include but are not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supranucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Parkinson's Disease, Wernicke-Korsakoff syndrome; chronic alcoholism; Creutzfeldt-Jakob disease; Subacute sclerosing panencephalitis hallerrorden-Spatz disease; and Dementia pugilistica. See, e.g., Berkow et. al., (eds.) (1987), The Merck Manual, (15$^{th}$) ed.), Merck and Co., Rahway, N.J.

The present invention is described in further detail in the following examples. The examples provided below are intended to be illustrative only, and are not intended to limit the scope of the invention.

EXAMPLES

Example 1

Production of Porcine Cells Heterozygous for the Alpha-1,3-GT Gene

Isolation and Transfection of Primary Porcine Fetal Fibroblasts.

Fetal fibroblast cells (PCFF4-1 to PCFF4-10) were isolated from 10 fetuses of the same pregnancy at day 33 of gestation. After removing the head and viscera, fetuses were washed with Hanks' balanced salt solution (HBSS; Gibco-BRL, Rockville, Md.), placed in 20 ml of HBSS, and diced with small surgical scissors. The tissue was pelleted and resuspended in 50-ml tubes with 40 ml of DMEM and 100 U/ml collagenase (Gibco-BRL) per fetus. Tubes were incubated for 40 min in a shaking water bath at 37° C. The digested tissue was allowed to settle for 3-4 min and the cell-rich supernatant was transferred to a new 50-ml tube and pelleted. The cells were then resuspended in 40 ml of DMEM containing 10% fetal calf serum (FCS), 1× nonessential amino acids, 1 mM sodium pyruvate and 2 ng/ml bFGF, and seeded into 10 cm. dishes. All cells were cryopreserved upon reaching confluence. SLA-1 to SLA-10 cells were isolated from 10 fetuses at day 28 of pregnancy. Fetuses were mashed through a 60-mesh metal screen using curved surgical forceps slowly so as not to generate excessive heat. The cell suspension was then pelleted and resuspended in 30 ml of DMEM containing 10% FCS, 1× nonessential amino acids, 2 ng/ml bFGF, and 10 µg/ml gentamycin. Cells were seeded in 10-cm dishes, cultured one to three days, and cryopreserved. For transfections, 10 µg of linearized vector DNA was introduced into 2 million cells by electroporation. Forty-eight hours after transfection, the transfected cells were seeded into 48-well plates at a density of 2,000 cells per well and were selected with 250 µg/ml of G418.

Knockout Vector Construction

Figure 6:
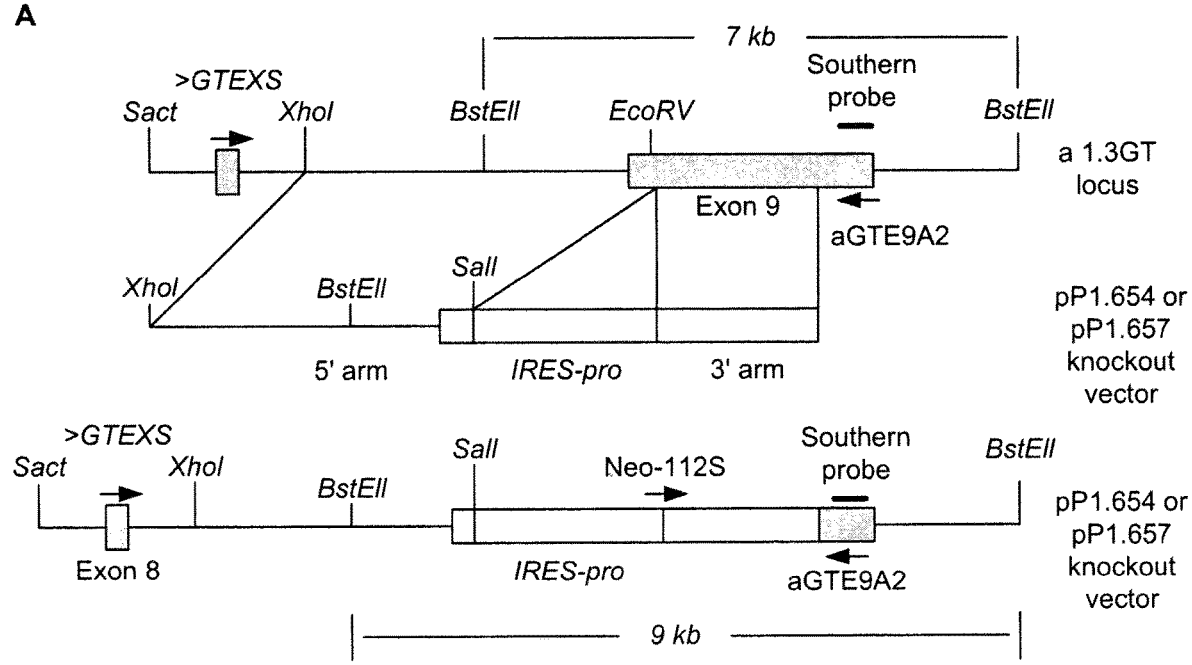
FIG. 6 is a diagram of the porcine alpha-1,3-GT locus, corresponding to alpha-1,3-GT genomic sequences that can be used as 5' and 3' arms in alpha-1,3-GT knockout vectors, and the structure of the targeted locus after homologous recombination. The names of names and positions of the primers used for 3'PCR and long-range PCR are indicated by short arrows. The short bar indicates the probe used for alpha-1,3-GT Southern blot analysis. The predicted size of Southern bands with BstEII digestion for both the endogenous alpha-1,3-GT locus and the alpha-1,3-GT targeted locus is also indicated.

Two alpha-1,3-GT knockout vectors, pPL654 and pPL657, were constructed from isogenic DNA of two primary porcine fetal fibroblasts, SLA1-10 and PCFF4-2 cells. A 6.8-kb alpha-1,3-GT genomic fragment, which includes most of intron 8 and exon 9, was generated by PCR from purified DNA of SLA1-10 cells and PCFF4-2 cells, respectively. The unique EcORV site at the 5' end of exon 9 was converted into a SalI site and a 1.8-kb IRES-neo-poly A fragment was inserted into the SalI site. IRES (internal ribosome entry site) functions as a translation initial site for neo protein. Thus, both vectors have a 4.9-kb 5' recombination arm and a 1.9-kb 3' recombination arm (FIG. 6).

3'PCR and Long-Range PCR

Approximately 1,000 cells were resuspended in 5 µl embryo lysis buffer (ELB) (40 mM Tris, pH 8.9, 0.9% Triton X-100, 0.9% NP40, 0.4 mg/ml Proteinase K), incubated at 65° C. for 15 min to lyse the cells and heated to 95° C. for 10 min to inactivate the Proteinase K. For 3' PCR analysis, fragments were amplified using the Expand High Fidelity PCR system (Roche Molecular Biochemicals) in 25 µl reaction volume with the following parameters: 35 cycles of 1 min at 94° C., 1 min at 60° C., and 2 min at 72° C. For LR-PCR, fragments were amplified by using TAKARA LA system (Panvera/Takara) in 50 µl reaction volume with the following parameters: 30 cycles of 10 s at 94° C., 30 s at 65° C., 10 min+20 s increase/cycle at 68° C., followed by one final cycle of 7 min at 68° C. 3'PCR and LR-PCR conditions for purified DNA was same as cells except that 1 µl of purified DNA (30 µg/ml) was mixed with 4 µl ELB.

Southern Blot Analysis of Cell Samples

Approximately 106 cells were lysed overnight at 60° C. in lysis buffer (10 mM Tris, pH 7.5, 10 mM EDTA, 10 mM NaCl, 0.5% (w/v) Sarcosyl, 1 mg/ml proteinase K) and the DNA precipitated with ethanol. The DNA was then digested with BstEII and separated on a 1% agarose gel. After electrophoresis, the DNA was transferred to a nylon membrane and probed with the 3'-end digoxigenin-labeled probe. Bands were detected using a chemiluminescent substrate system (Roche Molecular Biochemicals).

Results

Antibiotic (G418) resistant colonies were screened by 3' PCR with neo442S and αGTE9A2 as forward and reverse primers. Neo442S is at the 3' end of the neo gene and αGTE9A2 is at the 3' end of exon 9 in sequences located outside of the 3' recombination arm (FIG. 6). Therefore, only through successful targeting at the α1,3GT locus would the expected 2.4 kb PCR product be obtained. From a total of seven transfections in four different cell lines, 1105 G418 resistant colonies were picked, of which 100 (9%) were positive for α1,3 GT gene disruption in the initial 3' PCR screen (range 2.5-12%). Colonies 657A-A8, 657A-I6, and 657A-I11 showed the expected 2.4 kb band, while control PCFF4-6 cells, and another G418 resistant colony, 657A-P6, were negative. A portion of each 3' PCR positive colony was frozen down immediately, in several small aliquots, for future use in NT experiments, while the rest of cells were expanded for long-range PCR (LR-PCR) and Southern analysis.

Since PCR analysis to detect recombination junctions, or mRNA analysis (RT-PCR) can generate false positive results, a long-range PCR, which would encompass the entire targeted region, was performed. The LR-PCR covers the 7.4 kb α1,3GT genomic sequence from exon 8 to the end of exon 9, with both primers (αGTE8S and αGTE9A2) located outside of the recombination region (FIG. 2). The control PCFF4-6 cells, and the 3' PCR-negative colony, 657A-P6, showed only the endogenous 7.4 kb band from the wild-type α1,3GT locus. In contrast, three of the 3' PCR positive colonies, 657A-A8, 657A-I6 and 657A-I11, showed both the 7.4 kb endogenous band, and a new 9.2 kb band, of the size expected for targeted insertion of the 1.8 kb IRES-neo cassette into the α1,3GT locus.

Approximately half (17/30) of the LR-PCR positive colonies were successfully expanded to yield sufficient cell numbers (1×106 cells) for Southern analysis. It was anticipated that the colonies would be heterozygous for knockout at the α1,3 GT locus, and thus they should have one normal, unmodified gene copy, and one disrupted copy of the α1,3 GT gene. With BstEII digestion, the α1,3 GT knockout cells should show two bands: one 7 kb band of the size expected for the endogenous α1,3 GT allele, and a 9 kb band characteristic of insertion of the IRES-neo sequences at the α1,3 GT locus (FIG. 2). All 17 LR-PCR positive colonies were confirmed by Southern analysis for the knockout. The same membranes were re-probed with sequences specific for neo and the 9 kb band was detected with the neo probe, thus confirming targeted insertion of the IRES-neo cassette at the disrupted α1,3GT locus.

Example 2

Production of Porcine Cells Homozygous for the Alpha-1,3-GT Gene

Heterozygous alpha-1,3-GT knockout fetal fibroblasts, (657A-I11 1-6) cells, were isolated from a day-32 pregnancy as described above (See also Dai et al. Nature Biotechnology 20:451 (2002)). An ATG (start codon)—targeting alpha-1, 3-GT knockout vector was constructed (pPL680), which also contained a neo gene, to knock out the second allele of the alpha-1,3-GT gene. These cells were transfected by electroporation with pPL680 and selected for the alpha1, 3Gal-negative phenotype with purified *C. difficile* toxin A (described below).

Example 3

Selection with *C. difficile* Toxin A for Porcine Cells Homozygous for the Alpha-1,3-GT Gene Toxin A Cytotoxicity Curve Porcine cells (PCFF4-6) were exposed for 1 hour or overnight to ten-fold serial dilutions of toxin A (0.00001 µg/ml to 10 µg/ml). Cells were cultured in 24 well plates and were incubated with the toxin for 1 hour or overnight at 37° C. The results of this exposure are detailed in Table 2. Clearly, a 1 hour exposure to toxin A at >1 µg/ml resulted in a cytotoxic effect on >90% of the cells. A concentration of toxin A at or slightly above 1 µg/ml therefore was chosen for selection of genetically altered cells.

TABLE 2

Toxin A toxicity at 1 hour and overnight exposure

| [Toxin A], µg/ml | 1 hour incubation | Overnight incubation |
|---|---|---|
| 0 | 100% confluency | 100% confluency |
| .00001 | 100% confluency | 100% confluency |
| .0001 | 100% confluency | 100% confluency |
| .001 | 100% confluency | 100% confluency |
| .01 | 100% confluency | 50% confluency, 50% rounded |
| .1 | 90% confluency | Same as 10 ug/ml |
| 1 | >90% rounded Same as 10 ug/ml | |
| 10 | All cells rounded up | All cells rounded up, some lifted |

Disaggregated cells from a porcine embryo (I-11: 1-6) which contained a previously identified targeted knockout in one allele of the gal alpha-1,3-GT gene (Dai et al.) were transfected with 10 ug linearized vector DNA (promoter trap) by electroporation. After 48 hours, the cells were seeded into 48 well plates at a density of 2000 cells per well and selected with 250 ug/ml G418. Five days post-transfection, media was withdrawn from the wells, and replaced with 2 ug/ml toxin A in culture media (DMEM high glucose with 2.8 ng/ml bFGF and 20% FCS). Cells were exposed to the selective effect of toxin A for 2 hours at 37 C. The toxin A-containing media, along with any affected cells that have released from the plate surface, was withdrawn, the remaining cells washed with fresh media, and the media without toxin A replaced. Ten days later, cells were again exposed to toxin A at 1.3 ug/ml in media for 2 hours at 37 C. The media, toxin A, and any cells in solution were removed, the remaining cells washed, and the media replaced.

Sixteen days post-transfection, a single colony that exhibited toxin A insensitivity, designated 680B1, was harvested and a portion sent for DNA analysis and lectin staining. DNA analysis indicated that the toxin A insensitivity was not due to integration of the second target vector; however, the cells did not stain with GSL IB-4 lectin, indicating that a functional knockout of the locus had occurred. The 680B1 double knockout cells were used for nuclear transfer into 5 recipients and three pregnancies resulted. Two of these pregnancies spontaneously aborted in the first month; the four fetuses from the remaining pregnancy were harvested on day 39 of the pregnancy and the cells disaggregated and seeded into tissue culture. These fetal cells (680B1-1, 680B1-2, 680B1-3, 680B1-4) were exposed to toxin A at 1 ug/ml for 1 hour at 37 C, followed by medium removal, cell washing, and medium replacement without toxin A. Fetuses 1, 2, and 4 were not affected by toxin A, whereas most of the cells from fetus 3 rounded up, indicating that this embryo was sensitive to the cytotoxic effects of the toxin A.

Fetuses 1, 2, and 4 did not bind GS IB4 lectin, as indicated by FACS analysis (see Table 3), while fetus 3 did bind lectin. This suggests that fetuses 1, 2, and 4 do not carry the epitope alpha 1.3 gal for which this particular lectin is specific.

TABLE 3

FACS Results of 680B1-1 to 680B1-4 Cells with GS-IB4 Lectin
GS IB4 lectin positive cells (%)

| Cell | Unstaining | 50 μg/ml IB4 lectin | 100 μg/ml IB4 lectin |
| --- | --- | --- | --- |
| HeLa Cells (Negative CTL) | 1% | 2% | 2.8% |
| PCFF4-6 cells (Positive CTL) | 0.2% | 76% | 91% |
| PFF4 cells (Positive CTL) | 1.5% | 82% | 94% |
| 680B1-1 cells | 0.6% | 0.8% | 0.9% |
| 680B1-2 cells | 1.2% | 1.2% | 1.1% |
| 680B1-3 cells | 8% | 35% | 62% |
| 680B1-4 cells | 0.6% | 0.8% | 0.9% |

A complement fixation assay was run on cells from all four fetuses. The complement lysis assay was developed as a bioassay for lack of alpha gal expression. Human serum contains high levels of pre-formed antibody against alpha gal as well as the full portfolio of complement regulatory proteins (the C3 pathway). The presence of alpha gal on the surface of a cell, upon binding of anti-alpha gal antibody, activates the complement cascade, and results in complement-mediated cell lysis. Alpha-gal negative cells would be resistant to complement mediated lysis. In three separate tests, B1 and control pig cells were exposed to human serum plus complement, and assays performed to evaluate sensitivity or resistance to alpha-gal-initiated, complement-mediated cell lysis. The assay was performed with B1-1, B1-2, and B1-4 cells, as well as heterozygous GT KO cells (B1-3, gal positive), and with wild-type alpha-gal (+) PCFF4-6 pig cells as a control. Cells were exposed to one of three treatments; two negative controls, bovine serum albumin (BSA), and heat-inactivated human serum (HIA-HS) do not contain any functional complement protein and thus would not be expected to cause any significant cell lysis; the third treatment, non-heat-inactivated human serum (NHS) contains functional human complement as well as anti-gal specific antibodies, and thus would be expected to lyse cells which have galactose alpha 1,3 galactose on their cell surface.

The results shown in FIG. 1 clearly demonstrate that B1-1, B-2 and B 1-4 cells are resistant to human complement-mediated lysis while B 1-3 cells, which is a 1,3 Gal positive, is still as sensitive to human plasma as are wild-type PCFF4-6 cells.

Sequencing results of cDNA from all fetuses indicated that fetuses 1,2 and 4 contain a point mutation in the second alpha 1,3 GT allele, a change that could yield a dysfunctional enzyme (see FIG. 2). This mutation occurred at bp424 of the coding region, specifically, the second base pair of exon 9, of the alpha-1,3-GT (GGTA1) gene (GenBank Accession No. L36152) as a conversion of a thymine to a guanine residue, which results in an amino acid substitution of tyrosine at aa 142 to an aspartic acid.

Figure 3:
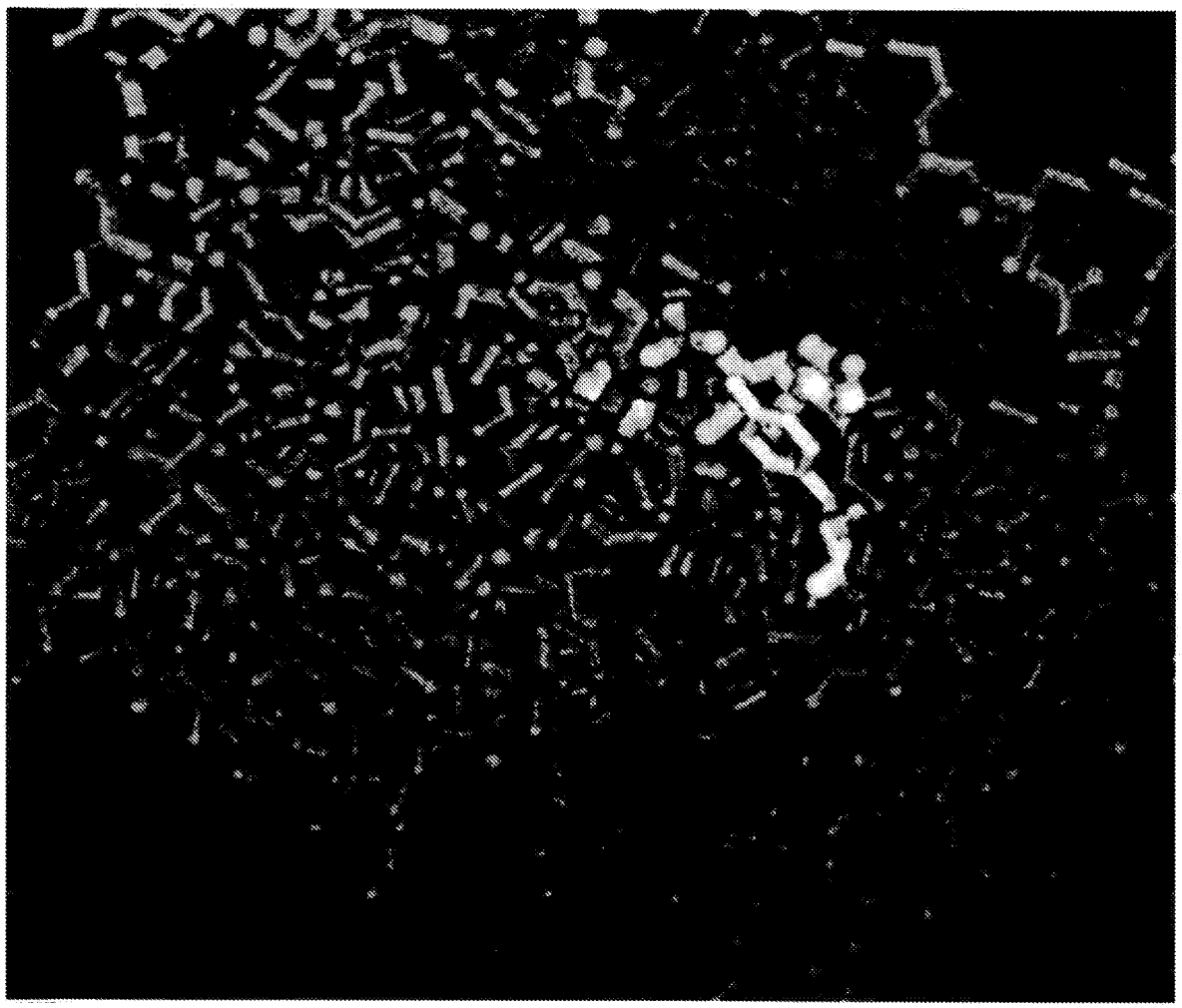
FIG. 3 is a representation of a 3-dimensional model of the UDP binding site of bovine alpha1,3GT. The aromatic ring of the tyrosine residue (foreground, white) can be seen in close proximity to the uracil base of UDP (grayscale).

This is a significant conversion, as the tyrosine, a hydrophilic amino acid, is a critical component of the UDP binding site of alpha 1,3GT (see FIG. 3). Analysis of the crystal structure of bovine alpha-1,3-GT protein showed that this tyrosine is the center of the catalytic domain of the enzyme, and is involved in UDP-Gal binding (Gastinel et. al., EMBO Journal 20(4): 638-649, 2001). Therefore, a change from tyrosine (a hydrophobic amino acid) to aspartic acid (a hydrophilic amino acid) would be expected to cause disruption of the αGT function (as observed).

To confirm that the mutated cDNA will not make functional αGT protein, the cDNAs from the second allele of all 4 cells were cloned into an expression vector and this GT expression vector transfected into human fibroblast cells (HeLa cells) as well as into primary Rhesus monkey cells. As humans and Old World monkeys lack a functional alpha 1,3 GT gene, the HeLa cells would not have an alpha 1,3 galactose on their cell surface (as assayed by lectin binding experiments). Results showed that the HeLa and monkey cells, when transfected with cDNA obtained from B1-1, B1-2 and B1-4 cells, were still α1,3 Gal negative by IB4-lectin staining, while Hela and Rhesus monkey cells transfected with cDNA from the B1-3, made a functional alpha 1,3 GT transcript and subsequently were α1,3Gal positive. Clearly, cells with the aspartate mutation (instead of tyrosine) cannot make functional alpha 1,3 galactosyl transferase Example 4

Figure 4:
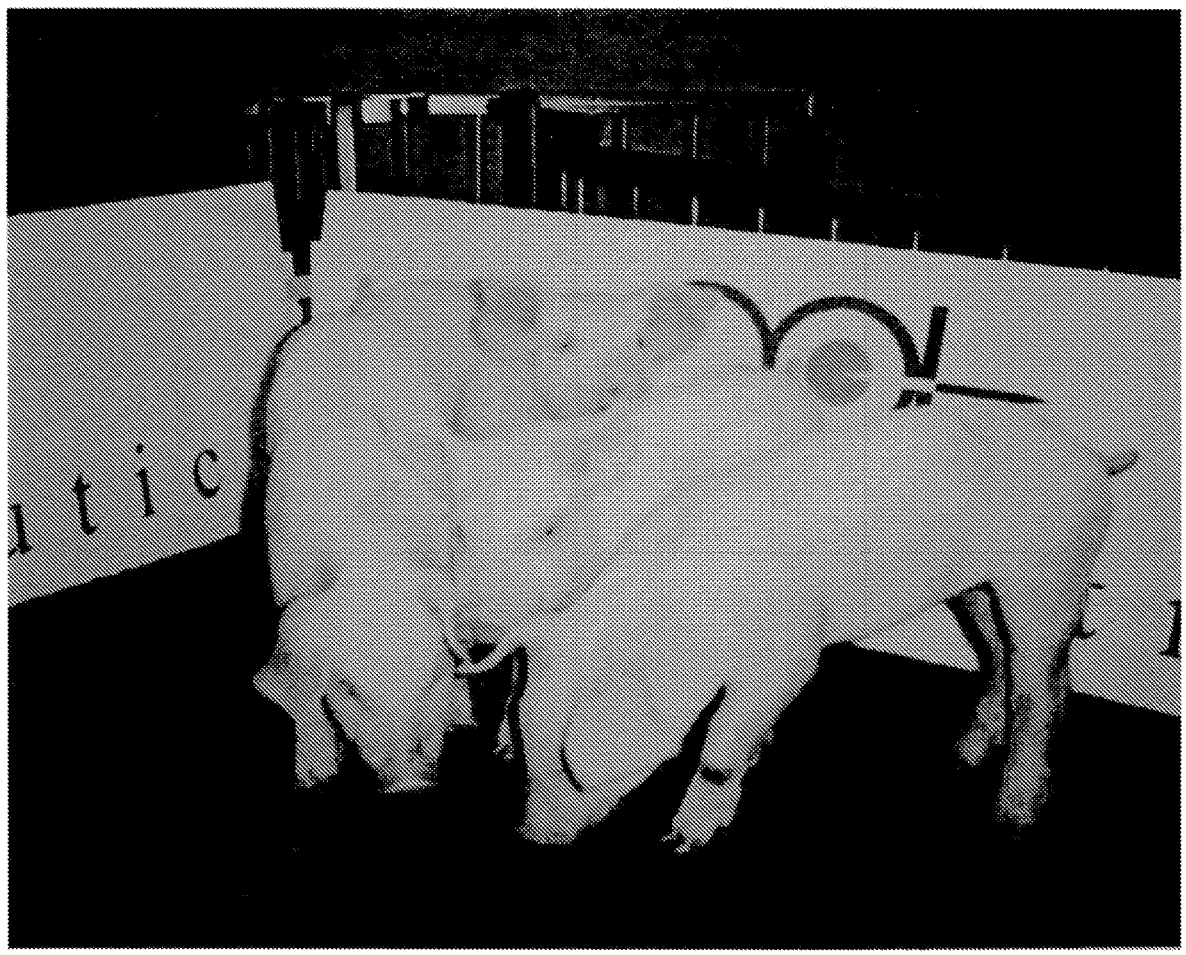
FIG. 4 is a photograph of homozygous, alpha-1,3-GT deficient cloned pigs produced by the methods of the invention, born on Jul. 25, 2002.

Generation of Cloned Pigs Using Homozygous Alpha 1,3 GT-Deficient Fetal Fibroblasts as Nuclear Donors Preparation of cells for nuclear transfer. Donor cells were genetically manipulated to produce cells homozygous for alpha 1,3 GT deficiency as described generally above. Nuclear transfer was performed by methods that are well known in the art (see, e.g., Dai et al., Nature Biotechnology 20: 251-255, 2002; and Polejaeva et al., Nature 407:86-90, 2000), using toxin A-selected porcine fibroblasts as nuclear donors that were produced as described in detail hereinabove Embryo transfers and resulting live births. In the initial attempt to produce live alpha-1,3-GT dKO pigs by nuclear transfer, a total of 16 embryo transfers were performed with genetically manipulated donor cells. Nine initial pregnancies were established but only two went beyond Day 75 of gestation. Five piglets were born on the Jul. 25, 2002. One piglet died immediately after birth and another four were born alive and appeared normal (FIG. 4).

Example 5

Analysis of Homozygous Alpha 1,3 GT Knockout Pigs

Tail fibroblast cells and umbilicus tissue sections were obtained from all 5 double knockout piglets and stained using the GS-IB4 lectin as described previously. No staining was observed, indicating a complete lack of galactose alpha 1,3 galactose epitope on the surface of tissues from these animals (data not shown). Aorta endothelial cells and muscle and tail fibroblasts isolated from the dead piglet (761-1) were negative with GS-IB4 lectin staining. FACS analysis of muscle fibroblasts from piglet 761-1 also showed a negative result for GS-IB4 binding. Tissue sections of liver, kidney, spleen, skin, intestine, muscle, brain, heart, pancreas, lung, aorta, tongue, umbilicus, and tail obtained from piglet 761-1 were all negative with GS-IB4 staining, indicating a complete lack of detectable cell surface alpha 1,3Gal epitopes (Phelps et al., Science 299: 411-414, 2003 including figure S3).

Figure 5:
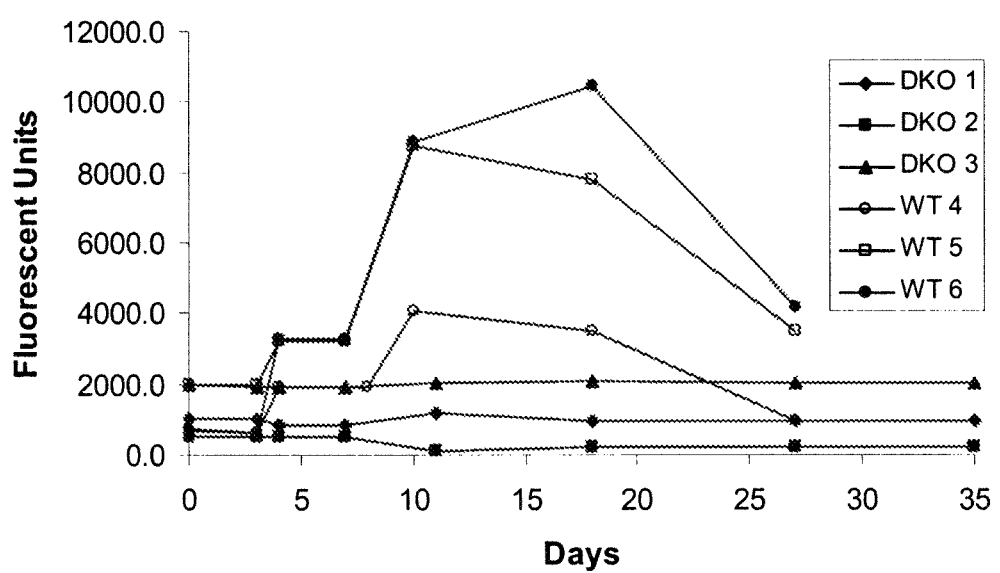
FIG. 5 is a graph depicting Anti-alpha-1,3-gal IgM levels before and after injections of piglet islet-like cell clusters (ICC) in alpha-1,3-GT KO mice. Each mouse received three serial ICC injections via i.p. (200-500 ICC per injection) over 4 days. All three recipients of wild-type (WT) piglet ICCs showed a significant elevation of anti-alpha 1,3Gal IgM titer and subsequent return to baseline 4 weeks after ICC implants. Sera from all three mice injected with alpha-1,3-GT DKO piglet ICCs maintained low baseline values of anti-alpha-1,3-gal IgM titer during the observation time of 35 days (Phelps et al., Science 299: 411-414, 2003, figure S4).

We performed an in vivo immunogenicity test with alpha 1,3GT-knockout mice. We injected islet-like cell clusters (ICCs) isolated from the pancreas of piglet 761-1 intraperitoneally into alpha 1,3GT knockout mice. We used ICCs from a neonatal wild-type piglet as a control. As shown in FIG. 5, no increase in the titer of immunoglobulin M (IgM) to alpha 1,3Gal was observed in alpha 1,3GT knockout mice after injection with ICCs from the alpha 1,3GT DKO piglet, in contrast to significant IgM titer increases observed in those mice injected with wild-type piglet ICCs (Phelps et al., Science 299: 411-414, 2003 including figure S4). This result clearly demonstrates that the DKO piglet cells do not make any alpha 1,3Gal epitopes.

Sequencing of DNA obtained from all five piglets confirmed the presence of the mutation at bp 424 of the GGTA1 gene, as observed in the 680B1-2 cells used to clone these animals (FIG. 2).

Since this first successful production of a litter of alpha-GT dKO pigs, two subsequent litters of dKO piglets have been produced by nuclear transfer, in one case (litter 662) using the dKO fetal fibroblasts as nuclear donor cells. Litter 660 was produced by nuclear transfer using tail fibroblast cells from a member of the litter 761 as nuclear donor. These births are summarized in Table 4.

TABLE 4

Summary of alpha-GT double knockout births produced by nuclear transfer

| Litter ID | Nuclear Donor | No. Births | Live Births |
|---|---|---|---|
| 761 | 680B: 1-2 | 5 | 4 |
| 662 | 680B: 1-2 | 1 | 0 |
| 660 | 761-5 | 4 | 2 |

Example 6

Breeding of Heterozygous Alpha 1,3 GT Single Knockout (SKO) Male and Female Pigs to Establish a Miniherd of Double Knockout (DKO) Pigs A total of 29 Southern blot confirmed cloned GT-SKO females and 25 Southern blot confirmed GT-SKO male cloned pigs have been generated to date. These male and female heterozygous (single gene alpha1,3GT knockout pigs) have been bred by natural breeding and by artificial insemination (AI), in order to generate a herd of DKO pigs for use in preclinical studies and human clinical trials. We have produced 16 alpha1,3-GT DKO piglets from 13 litters.

This invention has been described with reference to illustrative embodiments. Other embodiments of the general invention described herein and modifications there of will be apparent to those of skill in the art and are all considered within the scope of the invention.

What is claimed is:

1. A method for producing a porcine animal lacking expression of galactose alpha1,3-galactose, comprising: (a) exposing a population of porcine cells to *Clostridium difficile* (*C. difficile*) toxin A; (b) removing porcine cells that have an altered morphology upon exposure to *C. difficile* toxin A; (c) expanding and maintaining a porcine cell that does not have an altered morphology upon exposure to *C. difficile* toxin A to produce an expanded population of porcine cells; and (d) producing a porcine animal from one or more cells from the expanded population of porcine cells.

2. The method of claim 1, wherein porcine cells that have an altered morphology appear rounder as compared to the porcine cell that does not have an altered morphology.

3. The method of claim 1, wherein the population of porcine cells are on a plate matrix prior to exposure to the *C. difficile* toxin A.

4. The method of claim 3, wherein the porcine cells that have an altered morphology are released from the plate matrix upon exposure to the *C. difficile* toxin A.

* * * * *

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Exon 9: wild type amino acid sequence

<400> SEQUENCE: 1

Tyr Ile Glu His Tyr
1               5

<210> SEQ ID NO 2
<211> LENGTH: 27
<212> TYPE: DNA
<213> ORGANISM: Artificial Sequence
<220> FEATURE:
<223> OTHER INFORMATION: Exon 8-9: wild type DNA sequence

<400> SEQUENCE: 2
gctgtcggaa gatacattga gcattac                                            27
```

```
<210> SEQ ID NO 3
<211> LENGTH: 5
<212> TYPE: PRT
<213> ORGANISM: Artificial Sequence
<220> FEATURE:
<223> OTHER INFORMATION: Exon 9: mutated amino acid sequence

<400> SEQUENCE: 3

Asp Ile Glu His Tyr
1               5

<210> SEQ ID NO 4
<211> LENGTH: 27
<212> TYPE: DNA
<213> ORGANISM: Artificial Sequence
<220> FEATURE:
<223> OTHER INFORMATION: Exon 8-9: mutated DNA sequence

<400> SEQUENCE: 4
gctgtcggaa gagacattga gcattac                                       27
```